US005622827A

United States Patent [19]

McAllister et al.

[11] Patent Number: 5,622,827

[45] Date of Patent: Apr. 22, 1997

[54] **AMPLIFICATION PRIMERS AND NUCLEIC ACID PROBES TARGETED TO *COCCIDIOIDES IMMITIS* NUCLEIC ACID**

[75] Inventors: Diane L. McAllister, San Diego; Kathleen A. Clark, Cardiff-By-The-Sea, both of Calif.

[73] Assignee: Gen-Probe Incorporated, San Diego, Calif.

[21] Appl. No.: 384,541

[22] Filed: Feb. 7, 1995

[51] Int. Cl.[6] .............................. C12Q 1/68; C12P 19/34; C07H 21/02; C07H 21/04

[52] U.S. Cl. .............................. 435/6; 435/912; 536/24.3; 536/24.31; 536/24.32; 536/24.33

[58] Field of Search .............................. 536/24.3, 24.31, 536/24.32, 24.33; 435/62, 91.2

[56] References Cited

U.S. PATENT DOCUMENTS

| | | | |
|---|---|---|---|
| 4,689,295 | 8/1987 | Taber et al. | 435/6 |
| 5,030,557 | 7/1991 | Hogan et al. | 435/6 |
| 5,079,351 | 1/1992 | Sninsky et al. | 536/27 |
| 5,185,439 | 2/1993 | Arnold et al. | 536/24.3 |
| 5,283,174 | 2/1994 | Arnold et al. | 435/6 |
| 5,284,747 | 2/1994 | Milliman | 435/6 |

FOREIGN PATENT DOCUMENTS

| | | |
|---|---|---|
| 3138784 | 8/1994 | Australia . |
| 0133671 | 3/1985 | European Pat. Off. . |
| 0155359 | 9/1985 | European Pat. Off. . |
| 0313219 | 4/1987 | European Pat. Off. . |
| 0232085 | 8/1987 | European Pat. Off. . |
| 0245129 | 11/1987 | European Pat. Off. . |
| 0250662 | 1/1988 | European Pat. Off. . |
| 0277237 | 8/1988 | European Pat. Off. . |
| 8301073 | 3/1983 | WIPO . |
| 8402721 | 7/1984 | WIPO . |
| 8803957 | 6/1988 | WIPO . |
| WO93/22461 | 11/1993 | WIPO . |

OTHER PUBLICATIONS

Baroin et al, "Partial phylogeny of the unicellular eukaryotes based on rapid sequencing of a portion of 28S ribosomal RNA", Proc. Natl. Acad. Sci. 85:3474–3478 May 1988.

Padhye et al, "Comparative evaluation of chemiluminescent DNA probe assays and exoantigen tests for rapid identification of *Blastomyces dermatitidis* and *Coccidioides immitis*", J. Clin. Microbiol 32(4):867–870 Apr. 1994.

Sandhu et al, "Molecular probes for diagnosis of fungal infections", J. Clin. Microbiol. 33(11):2913–2919 Nov. 1995.

Pan et al, "Evidence for a phylogenetic connection between *Coccidioides immitis* and *Uncinocarpus reesii*", Microbiology 140:1481–1494 1994.

Stockman et al, "Evaluation of commercially available acridinium ester labeled chemiluminescent DNA probes for culture identification of *Blastomyces dermatitidis, Coccidioides immitis, Cryptococcus neoformans* and *Histoplasma capsulatum*", J. Clin. Microbio Apr. 1993.

Baess, "Deoxyribonucleic Acid Relationships Between Different Serovars of *Mycobacterium avium, Mycobacterium intracellulare* and *Mycobacteriaum scrofulaceum," Acta. Path. Microbiol. Immunol. Scand Sect B.* 91:201–203 (1983).

Baess, "Deoxyribonucleic Acid Relatedness Among Species of Rapidly Growing Mycobacteria," *Acta. Path. Microbiol. Immunol. Scand Sect B.* 90:371–375 (1982).

Baess and Bentzon, "Deoxyribonucleic Acid Hybridization Between Different Species of Mycobacteria," *Acta. Path. Microbiol. Scand Sect. B* 86:71–76 (1978).

*Bergy's Manual of Systematic Bacteriology,* "Differentation of the genus Legionella from other taxa," 1:283 (1984).

*Bergy's Manual of Systematic Bacteriology,* "Gram–Negative Aerobic Rods and Cocci," 1:160 (1984).

Boddinhaus et al., "Detection and Identification of Mycobacteria by Amplification of rRNA," *J. Clinical Microbiology* 28:1751–1759 (1990).

Bradley, "Relationships Among Mycobacteria and Nocardiae Based upon Deoxyribonucleic Acid Reassociation," *J. Bacteriology* 113:645–651 (1973).

Brenner et al., "Classification of the Legionnaires' Disease Bacterium: An Interim Report," *Current Microbiology* 1:71–75 (1978).

Brenner et al., "Classification of the Leginnaires' Disease Bacterium: *Legionella pneumophila,* genus novum, species *nova,* of the Family Legionellaceae, familia nova," *Annals of Internal Medicine* 90:656–658 (1979).

Brenner, "Ten New Species of *Legionella," International Journal of Systematic Bacteriology* 35:50–59 (1985).

Brenner, "DNA Hybridization for Characterization, Classification, and Identification of Bacteria," in *Nucleic Acid and Monoclonal Antibody Probes,* ed. Bala Swaminathan and Gyan Prakash (New York:Marcel Dekker, Inc., 1989) pp. 75–104.

Brenner, "Facultatively Anaerobic Gram–Negative Rods," from *Bergy's Manual of Systematic Bacteriology* 1:408–410 (1984).

Brenner, "Deoxyribonucleic Acid Reassociation in the Taxonomy of Enteric Bacteria," *Int. J. Systematic Bacteriology* 23:298–307 (1973).

Brosius et al., "Complete nucleotide sequence of a 16S ribosomal RNA gene from *Escherichia coli," Proc. Natl. Sci. USA* 75:4801–4805 (1978).

Brosius et al., "Complete nucleotide sequence of a 23S ribosomal RNA gene from *Escherichia coli," Proc. Natl. Acad. Sci. USA* 77:201–204 (1980).

(List continued on next page.)

*Primary Examiner*—Stephanie W. Zitomer
*Assistant Examiner*—Jeffrey Fredman
*Attorney, Agent, or Firm*—Lyon & Lyon

[57] ABSTRACT

The present invention describes oligonucleotides targeted to *Coccidioides immitis* nucleic acid sequences which are particularly useful to aid in detecting *Coccidioides immitis.* The oligonucleotides can aid in detecting *Coccidioides immitis* in different ways such as by acting as hybridization assay probes, and/or amplification primers.

40 Claims, No Drawings

OTHER PUBLICATIONS

Carbon et al., "The sequence of the 16S RNA from Proteins vulgaris. Sequence comparison with *E. coli* 165 RNA and its use in secondary structure model building," *Nucleic Acids Research* 9;2325–2333 (1981).
Carmichael and Parikh, "Multiple Pneumonias in a Man Infected with HIV," *The Journal of Family Practice* 37:610–615 (1993).
Clark, "Ch. 15 –Coccidioidomycosis" in *Medical Mycology*, Kwon–Chung and Bennett, Lea and Feibeger Publishers, Philadelphia/London (1992) pp. 356–390.
Check, W.A., *CAP Today*, 1:12–16 (Aug. 1994).
*Clinical Microbiology Newsletter* 9:90–91 (1987).
Colwell et al., "Numerical Taxonomy and Deoxyribonucleic Acid Reassociation in the Taxonomy of Some Gram–Negative Fermentative Bacteria," *International Journal of Systematic Bacteriology* 24:422–433 (1974).
Crosa et al., "Polynucleotide Sequence Divergence in the Genus Citrobacter," *J. General Microbiology* 83:271–282 (1974).
Drake et al., "Rapid Identification of *Mycobacterium avium* complex in Culture Using DNA Probes," *J. Clinical Microbiology* 25:1442–1445 (1987).
Festl et al., "DNA hybridization Probe for the *Pseudomonas fluroescens* Group," *Applied and Environmental Microbiology* 52:1190–1194 (1986).
GenProbe Product Description for *ACCUPROBE* pp. 1–5.
Göbel et al., "Oligonucleotide Probes Complementary to Variable Regions of Ribosomal RNA Discriminate between *Mycoplasma* Species," *Journal of General Microbiology* 133:1969–1974 (1987).
Göbel and Stanbridge, "Cloned Mycoplasm Ribosomal RNA Genes for the Detection of Mycoplasma Contamination in Tissue Cultures," *Science* 226:1211–1213 (1984).
Goldin, "Ch. 20 –Medical Mycology," in *Clinical Diagnosis by Laboratory Methods*, Davidsohn and Henry eds., W.B. Saunders Company (1974) pp. 1118–1150.
Goodfellow and Minnikin, "Circumscription of the Genus," *The Mycobacteria*, pp. 1–24, Kubica and Wayne eds. (Dekker: New York, 1984).
Goodfellow and Wayne in *The Biology of the Mycobacteria* Ralledge & Stanford eds. (Acad Press 1982) 1:476–479.
Grimont et al., "DNA Probe Specific for *Legionella pneumophila*," *J. Clinical Microbiology* 21:431–437 (1985).
Harvey and Greenwood, "Relationships Among Catalase–Positive Campylobacters Determined by Deoxyribonucleic Acid–Deoxyribonucleic Acid Hybridization," *International Journal of Systematic Bacteriology* 33:275–284 (1983).
Imaeda, "Deoxyribonucleic Acid Relatedness Among Selected Strains of Mycobacterium tuberculosis, Mycobacterium bovis, Mycobacterium bovis BCG, Mycobacterium microti, and Mycobacterium africanum," *International Journal of Systematic Bacteriology* 35:147–150 (1985).
Jonas, et al., *Detection and Identification of Mycobacterium tuberculosis Directly from Sputum Sediments by Amplification of rRNA*, pp. 2410–2416 (1993).
Jones and Collins, "Irregular, Nonsporing Gram–Positive Rods," *Bergy's Manual of Systematic Bacteriology* 2:1261–1266 (1986).
Killian, "A Taxonomic Study of the Genus Haemophilus, with the Proposal of a New Species," *J. General Microbiology* 93:9–62 (1976).
Kilpper–Balz et al., "Nucleic Acid Hybridization of Group N and Group D Streptococci," *Current Microbiology* 7:245–250 (1982).
Kilpper–Balz and Schleifer, "DNA–rRNA Hybridization Studies Among *Staphylococci* and Some Other Gram–Positive Bacteria," *FEMS Microbiology Letters* 10:357–362 (1981).
Kohne et al., "Nucleic Acid Probe Specific for Members of the Genus Legionella," in *Proceedings of the Second International Symposium, American Society for Microbiology*, C. Thornsbury, A. Balows, J.C. Freeley, and W. Jakukowski eds. (Washington, d.C.) pp. 107–108.
Kohne, "Application of DNA probe tests to the diagnosis of infectious disease," *American Clinical Products Review*, Nov. (1986).
Lane et al., "Rapid determination of 16S ribosomal RNA sequences for phylogenetic analyses," *Proc. Natl. Acad. Sci. USA* 82:6955–6959 (1985).
Lau et al., "Phylogenetic Diversity and Position of the Genus Campylobacter," *System App. Microbiol.* 9:231–238 (1987).
Leclerc et al., "Phylogeny of dermatophytes and dimorphic fungi based on large subunit ribosomal RNA sequence comparisons," *Journal of Medical and Veterinary Mycology* 32:331–341 (1994).
Ludwig and Stackebrandt, "A phylogenetic analysis of *Legionella*," *Archives of Microbiology* 135:45–50 (1983).
Malouin et al., "DNA Probe Technology for Rapid Detection of *Haemophilus influenzae* in Clinical Specimens," *J. Clin. Microbiology* 26:2132–2138 (1988).
McCarroll et al., "Nucleotide Sequence of the Dictyostelium discoideum Small–Subunit Ribosomal Ribonucleic Acid Inferred from the Gene Sequence: Evolutionary Implications," *Biochemistry* 22:5858–5868 (1983).
Miller, et al., Evaluation of Gen–Probe Amplified Mycobacterium Tuberculosis Direct Test and PCR for Direct Detection of *Mycobacterium tuberculosis* in Clinical Specimens, J. Clin. Micro. 32:393–397 (1994).
Mordarski et al., "Ribosomal Ribonucleic Acid Similarities in the Classification of *Rhodococcus* and Related Taxa," *Journal of General Microbiology* 118:313–319 (1980).
Musser et al., "Genetic Relationships of Serologically Nontypable and Serotype b Strains of *Haemophilum influenzae*," *Infection and Immunity* 52:183–191 (1986).
Razin, "Molecular and Biological Feature of Mycoplasmas (Mollicutes)," *Microbiol. Rev.* 49:419–455 (1985).
Razin et al., "Molecular and Biological Features of Mollicutes (Mycoplasmas)", *Ann. Microbiol.* 135:9–15 (1984).
Reddy, et al., "Specific amplification of *Aspergillus fumigatus* DNA by polymerase chain reaction," *Mol. Cell. Probes* 7:121–126 (1993).
Rogall et al., "Differentiation of Mycobacterium species by dfirect sequencing of amplified DNA," *J. Gen. Microbiology* 136:1915–1920 (1990).
Rogall et al., "Towards a Phylogeny and Definition of Species at the Molecular Level within the Genus Mycobactyerium," *International Journal of Systematic Bacteriology* 40:323–330 (1990) Incomplete.
Rogers et al., "Construction of the mycoplasma evolutionary tree from 5S rRNA sequence data," *Proc. Natl. Acad. Sci. USA* 82:1160–1164 (1985).
Saxe and Kimmel, "SAS1 and SAS2, GTP–Binding Protein Genes in *Dictyostelium discoideum* with Sequence Similarities to Essential Genes in *Saccharomyces cerevisiae*," *Molecular and Cellular Biology* 10:2367–2378 (1990).

Schleifer and Kilpper–Balz, "Transfer of Streptococcus faecalis and Streptococcus faecium to the Genus Enterococcus nom. rev. as Enterococcus faecalis comb. nov. and enterococcus faecium cobm. nov.," *Int'l J. System. Bact.* 34:31–34 (1984).

Stackebrandt and Schleifer, "Molecular Systematics of Actinomycetes and Related Organisms," *Biological, Biochemical and Biomedical aspects of Actinomycetes* pp. 485–504 (1984).

Stahl and Urbance, "The Division between Fast–and Slow––Growing Species Corresponds to Natural Relationships among the *Mycobacteria,*" *Journal of Bacteriology* 172:116–124 (1990).

Stahl, "Evolution, Ecology and Diagnosis: Unity in Variety," *Biotechnology* 4:623–628 (1986).

Veldman et al., "The primary and secondary structure of yeast 26S rRNA," *Nucleic Acids Research* 9:6935–6953 (1981).

Weisburg et al., "A Phylogenetic Analysis of the Mycoplasmas: Basis for Their Classification," *Journal of Bacteriology* 171:6455–6467 (1989).

Yogev and Razin, "Common Deoxyribonucleic Acid Sequences in Mycoplasma genitalium and Mycoplasma pneumoniae Genomes," *Int'l J. System. Bacter.* 35:426–430 (1986).

AMPLIFICATION PRIMERS AND NUCLEIC ACID PROBES TARGETED TO *COCCIDIOIDES IMMITIS* NUCLEIC ACID

FIELD OF THE INVENTION

This invention relates to the design and use of oligonucleotides targeted to *Coccidioides immitis* nucleic acid. Different types of oligonucleotides are described including hybridization assay probes, helper probes, and amplification oligonucleotides. The oligonucleotides are particularly useful for detecting the species *Coccidioides immitis* in test samples, such as from sputum, tissue samples, body fluids, experimental solutions and cultures.

BACKGROUND OF THE INVENTION

*Coccidioides immitis* is the etiologic agent of the fungal disease coccidioidomycosis (San Joaquin Valley Fever). Infection in man and other animals usually occurs following inhalation of arthroconidia into the lungs. Disease may be evident after an incubation period of one to four weeks. Approximately 60 percent of those infections are asymptomatic or characterized by a self-limiting upper respiratory infection. The remaining 40 percent of infections proceed to the lower respiratory tract resulting in mild or severe pneumonia which may resolve spontaneously or progress to form pulmonary nodules or cavities, occasionally resembling tuberculosis or carcinoma. In rare cases, the infection may disseminate to almost any organ of the body, including the skin, bone and central nervous system. Recent increases in infections by fungal pathogens, including *Coccidioides immitis* have increased the need for a rapid and sensitive method of detection for *Coccidioides immitis*. See William A. Check, CAP Today, Aug. 1994, 1, 12–16.

Conventional laboratory identification methods used to identify *C. immitis* include culture on fungal media, growth rate, colony morphology, microscopic morphology, animal inoculation and biochemical tests. These tests may require long incubation periods and require additional confirmatory tests. Identification begins with culture of the specimen on fungal media. The time required for growth to a visible, cobweb-like colony varies from 3 to 21 days and the mature colony morphology varies. Additional growth is needed before the characteristic microscopic sporulation pattern of alternating arthroconidia may be seen. Many species of fungi other than *C. immitis* may produce similar colony and sporulation patterns, including such naturally occurring soil fungi as Malbranchea and Uncinocarpus spp. Some yeast-like organisms such as Geotrichum and Trichosporon spp. may also resemble *C. immitis*.

Animal inoculation is another method sometimes used to detect *Coccidioides immitis* by producing the species-specific spherules characteristic of *Coccidioides immitis*. Still other confirmatory tests based on exoantigen extraction have been described, but these tests may take 3 to 5 days or longer to perform.

None of the references herein are admitted to be prior art.

SUMMARY OF THE INVENTION

This invention concerns oligonucleotides targeted to *Coccidioides immitis* nucleic acid sequences, and methods of detecting *Coccidioides immitis*. Hybridization assay probes, amplification primers, and helper probes are described. Hybridization assay probes can preferentially hybridize under stringent hybridization assay conditions to a *Coccidioides immitis* nucleic acid target region to form a detectable duplex indicating the presence of *Coccidioides immitis* in a test sample. Amplification primers can be used to prime amplification reactions producing *Coccidioides immitis* target nucleic acid which can be detected by the probes described herein. Also featured are probe mixes for use in hybridization assays for the detection of *Coccidioides immitis*.

In a first aspect, the invention features a hybridization assay probe having one of the following sequences:

SEQ ID NO:21: GCGCCACGGC ATAAGTTCCT TG,

SEQ ID NO:22: CAAGGAACTT ATGCCGTGGC GC,

SEQ ID NO:23: GCGCCACGGC AUAAGUUCCU UG,

SEQ ID NO:24: CAAGGAACUU AUGCCGUGGC GC.

The probe can distinguish *Coccidioides immitis* from closely related phylogenetic neighbors, by preferentially hybridizing to a *Coccidioides immitis* target nucleic acid sequence region under stringent hybridization assay conditions. The hybridization assay probe is useful for detecting the presence of *Coccidioides immitis* and/or for determining the quantity of *Coccidioides immitis* present in a test sample, e.g., samples of sputum, urine, blood, tissue sections, food, soil and water. Other hybridization probes to the 28S rRNA subunit of *Coccidioides immitis* have been previously described in Milliman, U.S. Pat. No. 5,284,747 (not admitted to be prior art).

Probes contain a nucleotide sequence perfectly complementary, or substantially complementary, to a *Coccidioides immitis* target sequence. Hybridization assay probes are sufficiently complementary to nucleic acid containing a target sequence to form a detectable hybrid probe:target duplex under stringent hybridization assay conditions. A hybridization assay probe is preferably between 15 and 100 nucleotides in length, more preferably between 15 and 50 nucleotides in length. Even more preferably the probe is between 15 and 25 nucleotides in length.

Hybridization assay probes are preferably labeled with a reporter group moiety such as a radioisotope, a fluorescent moiety, a chemiluminescent moiety, an enzyme, or a ligand, incorporated into the probe. The moiety can be used to detect or confirm probe hybridization to its target sequence.

By "preferentially hybridize" is meant that under stringent hybridization assay conditions, hybridization assay probes can hybridize to their target nucleic acids to form stable probe:target hybrids indicating the presence of the target nucleic acid and do not form a sufficient number of stable probe:non-target hybrids to indicate the presence of a closely related non-target nucleic acid. Thus, the probe hybridizes to target nucleic acid to a sufficiently greater extent than to non-target nucleic acid to enable one skilled in the art to accurately detect the presence of *Coccidioides immitis* and distinguish its presence from that of a closely related organism.

Organisms "closely related" to *Coccidioides immitis* include *Malbranchea albolutea, Blastomyces dermatitidis, Candida parapsilosis, Histoplasma capsulatum, Auxarthron thaxteri, Gymnoascus dugwayensis, Aspergillus flavus, Myxotrichum deflexum, Aspergillis niger, Candida krusei, Candida glabrata, Aspergillis fumigatus, Arachnioites flavoluteus, Oidiodendron echinulatum, Candida albicans*, and *Malbranchea dendriticus*. The most clinically important, closely related organisms are *Blastomyces dermatitidis* and *Histoplasma capsulatum*.

Another aspect of the present invention relates to compositions containing a nucleic acid hybrid made up of a hybridization assay probe and a *Coccidioides immitis* nucleic acid molecule having a nucleic acid sequence substantially complementary thereto. The hybrid is a stable nucleic acid structure comprising a double-stranded, hydrogen-bonded region, preferably 15 to 100 nucleotides in length. Such hybrids include RNA:RNA, RNA:DNA, or DNA:DNA duplex molecules. The hybridization probe present in the nucleic acid hybrid will contain one of the following sequences: SEQ ID NOs: 21–24.

Substantially complementary means that the nucleic acid sequence is able to preferentially hybridize under stringent hybridization assay conditions to a target nucleic acid region. Preferably, the probe has a region of 9 out of 10 bases which are complementary to the corresponding target region. More preferably, the probe has a region of 14 out of 17 bases which are complementary to the corresponding target region.

Another aspect of the invention features probe mixes containing a hybridization probe and a helper probe for use in a hybridization assay. Helper probes can be used to facilitate hybridization of a hybridization assay probe to its target sequence region. Helper probes facilitate hybridization by enhancing the kinetics and/or the Tm of the target:hybridization probe duplex. Helper probes are generally described in Hogan and Milliman, U.S. Pat. No. 5,030,557, which is hereby incorporated by reference herein. In a preferred embodiment, the helper oligonucleotides of the probe mixes comprise, consist essentially of, consist of or are substantially similar to the helper probe sequence:

SEQ ID NO:25: GAACAGGACG TCATAGAGGG TGAGAATCC or its RNA equivalent (SEQ ID NO:27). The hybridization assay probe of the probe mix will contain one of the following sequences: SEQ ID NOs: 21–24.

"RNA and DNA equivalent nucleotides" refer to RNA and DNA molecules having the equivalent base pair hybridization properties. RNA and DNA equivalents have different sugar groups (i.e., ribose versus deoxy ribose), and may differ by the presence of uracil in RNA and thymine in DNA. The difference between RNA and DNA equivalents do not contribute to differences in substantially similar nucleic acid sequences.

With respect to a hybridization assay probe or a helper probe, a "substantially similar" nucleotide sequence is a nucleotide sequence identical to, or having no more than a 10% nucleotide base difference than an identified nucleotide sequence (excluding substitution of a RNA or DNA equivalent nucleotide, e.g., substituting T for U or U for T) and which enables the probe to hybridize to *Coccidioides immitis* nucleic acid under stringent hybridization conditions used to detect *Coccidioides immitis*. With respect to amplification oligonucleotides, a "substantially similar" nucleotide sequence is a nucleotide sequence identical to, or having no more than a 10% nucleotide base difference than an identified nucleotide sequence (excluding substitution of a RNA or DNA equivalent nucleotide) and which enables an amplification oligonucleotide to prime the amplification of *Coccidioides immitis* target nucleic acid under amplification conditions. In alternate embodiments, substantially similar for a hybridization assay probe, helper probe, or amplification oligonucleotide refers to a 5% difference in complementarity to an oligonucleotide containing a particular nucleotide sequence.

The phrases "consists essentially of" or "consisting essentially of" mean that the oligonucleotide has a nucleotide sequence substantially similar to a specified nucleotide sequence and is preferably no more than four additional nucleotides longer or two nucleotides shorter. Thus, these phrases contain both a sequence length limitation and a sequence variation limitation. Any additions or deletions are non-material variations of the specified nucleotide sequence which do not prevent the oligonucleotide from having its claimed property. For instance, with respect to hybridization probes and helper probes, any additions or deletions would not prevent the hybridization probes or helper probes from being able to preferentially hybridize under stringent hybridization assay conditions to its target nucleic acid over non-target nucleic acids. With respect to an amplification oligonucleotide, any additions or deletions would not prevent the amplification oligonucleotide from being able to hybridize to *Coccidioides immitis* nucleic acid under amplification conditions, or to prime amplification reactions producing target *Coccidioides immitis* nucleic acid under amplification conditions.

In another aspect, the invention features amplification oligonucleotides useful for amplifying *Coccidioides immitis* target regions. Amplification oligonucleotides are preferably 15 to 100 nucleotides in length, more preferably 15 to 60 nucleotides. Amplification oligonucleotides may have modifications, such as blocked 3' termini.

Amplification oligonucleotides can act as primers and may be part of promoter-primer combinations, i.e., a primer having a specific nucleic acid sequence attached to the 5' terminus that is recognized by an RNA polymerase (including, but not limited to, the promoter sequence for T7, T3, or SP6 RNA polymerase, or sequences enhancing initiation or elongation of RNA transcription by an RNA polymerase). One example of a promoter sequence includes the sequence SEQ ID NO: 41 5'-AATTTAATAC GACTCACTAT AGGGAGA-3'. Other examples of useful promoter sequences are contained in various commercially available vectors including, for example, pBluescript® vectors from Stratagene Cloning Systems or the pGEM™ vectors from Promega Biotec.

Preferably, amplification oligonucleotides contain a primer sequence having, consisting essentially of, consisting of, or substantially similar to one of the following sequences:

SEQ ID NO:9: GCTCAAATTT GAAATCTGTC CATGCGGAGC

SEQ ID NO:11 (RNA equivalent to SEQ ID NO:9),

SEQ ID NO:29: GTCCAGCAGC CACAGACGGG ATTC,

SEQ ID NO:31 (RNA equivalent to SEQ ID NO:29),

SEQ ID NO:33: CACAGACGGG ATTCTCACCC TC,

SEQ ID NO:35 (RNA equivalent to SEQ ID NO:33),

SEQ ID NO:37: GGATTCTCAC CCTCTATGAC GTCCTG, and

SEQ ID NO:39 (RNA equivalent to SEQ ID NO:37).

More preferably, the amplification oligonucleotide will contain a primer sequence corresponding to SEQ ID NOs: 33, 35, 37, 39. Even more preferably, the amplification oligonucleotide will contain a primer sequence corresponding to SEQ ID NOs: 37, 39.

Examples of amplification oligonucleotides having a promoter sequence are:

SEQ ID NO:1: AATTTAATAC GACTCACTAT AGGGAGAGTC CAGCAGCCAC AGACGGGATT C,

SEQ ID NO:5: AATTTAATAC GACTCACTAT AGGGAGACAC AGACGGGATT CTCACCCTC, and

SEQ ID NO:13: AATTTAATAC GACTCACTAT AGGGAGAGGA TTCTCACCCT CTATGACGTC CTG.

More preferably, amplification oligonucleotides have, consist essentially of, consist or, or are substantially similar to, sequences provided by SEQ ID NOs: 5, 13. Even more preferably, amplification oligonucleotides have or consist essentially of sequences provided by SEQ ID NO: 13.

Amplification oligonucleotides can be used in nucleic acid amplification procedures, such as the polymerase chain reaction or Transcription Mediated Amplification reaction using RNA polymerase, DNA polymerase and RNaseH or its equivalent, as described by Kacian and Fultz supra, hereby incorporated by reference herein. In addition, other methods of making use of transcription in amplification assays are described in Sninsky et al., U.S. Pat. No. 5,079, 351.

Amplification oligonucleotides hybridize with a target nucleic acid and may act as a primer for nucleic acid synthesis. The oligonucleotides amplified by extension of the primers will be complementary to the hybridization assay probe. Preferably, promoters which are recognized by an RNA polymerase such as T7, T3 or SP6 RNA polymerase are used for the transcription-based amplification.

Amplification means increasing the number of nucleic acid molecules having at least one target nucleic acid sequence complementary to a hybridization assay probe. In order to increase the amplification of oligonucleotides containing target sequences, amplification preferably includes the production of target-template strands containing a double-stranded promoter region to serve as templates for RNA polymerase.

In other aspects, methods are described for using the hybridization assay probes, helper probes and amplification oligonucleotides to detect *Coccidioides immitis* and to distinguish *Coccidioides immitis* from closely related organisms. These amplification assays preferably involve amplifying target nucleic acid in a sample to be tested, contacting the amplified sequences under stringent hybridization assay conditions with a hybridization assay probe which preferentially hybridizes with *Coccidioides immitis* nucleic acid over nucleic acids present in closely related organisms, and measuring the amount of hybridized probe.

The sample is preferably food, soil, or water; a clinical sample such as sputum, urine, blood, or tissue sections; or nucleic acid isolated from a cultured sample. More preferably, the amplification assay will be used to detect *Coccidioides immitis* directly from a clinical sample. Detection directly from a clinical sample means that culture of the sample on fungal media is not carried out prior to detection or amplification.

Preferably the amplification assay utilizes a hybridization probe consisting of one of the following sequences: SEQ ID NOs:17–24. Helper probes for use in preferred embodiments of the amplification assay have, or are substantially similar to SEQ ID NO:25 and SEQ ID NO:27. Amplification oligonucleotides which can be used in preferred embodiments of the amplification assay have, consist essentially of, consist of, or are substantially similar to SEQ ID NOs:1, 5, 13. More preferably, the amplification oligonucleotides used in the amplification assay will have, consist essentially of, consist of, or are substantially similar to SEQ ID NOs: 5, 13. Even more preferably, the amplification oligonucleotides used in the amplification assay will have, consist essentially of, consist of, or will be substantially similar to SEQ ID NOs:13. In other embodiments, the amplification oligonucleotides will preferably have, consist essentially of, consist of, or be substantially similar to SEQ ID NOs:9, 11, 29, 31, 33, 35, 37, 39; in addition, these amplification oligonucleotides will preferably contain a nucleic acid sequence to the 5' terminus which is a promoter for an RNA polymerase, preferably T7 RNA polymerase. Even more preferably this added nucleic acid sequence will consist essentially of SEQ ID NO:41.

The oligonucleotides targeted to *Coccidioides immitis* offer a rapid, non-subjective method of identification and quantitation of *Coccidioides immitis* by detecting the presence of specific nucleic acid sequences unique to different species and strains of *Coccidioides immitis*. The probes of this invention can be used in hybridization assays to identify *Coccidioides immitis* isolated from culture in less than an hour. Furthermore, use of an amplification step allows detection of *C. immitis* directly from clinical samples in less than three hours.

Combining an amplification step with a hybridization assay in the amplification assay increases the amount of target and can thus eliminate the need for culturing *C. immitis* and its inherent risk of infection to laboratory workers. If a hybridization assay or amplification assay is performed in conjunction with culture tests, the assay can warn laboratory workers of the presence of *C. immitis* in a culture sample.

Other features and advantages of the invention will be apparent from the following description of the preferred embodiments thereof, and from the claims.

DESCRIPTION OF THE PREFERRED EMBODIMENTS

Described herein are preferred sequences for hybridization assay probes, helper probes, and amplification oligonucleotides designed to hybridize to target sequences in *Coccidioides immitis* rRNA or rDNA. In addition, preferred mixes of hybridization assay probes and helper probes useful for detecting *Coccidioides immitis* are described. Also described are hybrids formed by a hybridization assay probe and a target sequence. Preferred methods for using the probes and amplification oligonucleotides to detect *Coccidioides immitis* are included in this description.

I. Construction and Use of Hybridization Assay Probes.

A. Obtaining rRNA Sequences

With the exception of viruses, all prokaryotic organisms contain rRNA genes encoding RNA homologous to 5S rRNA, 16S rRNA and a larger rRNA molecule known as 23S rRNA. In the eukaryotes these rRNA molecules are the 5S rRNA, 18S rRNA and 28S rRNA which are substantially similar to the prokaryotic molecules. Milliman, U.S. Pat. No. 5,284,747, previously described nucleic acid probes complementary to particular 28S rRNA sequences obtained from *Coccidioides immitis*, and is hereby incorporated by reference herein.

Sequence information was obtained experimentally and from published information. (See Weisburg, et al., *J. Bacteriol* 171:6455 (1989).) Experimental information was obtained by isolating and sequencing rRNA from various organisms using standard techniques known in the art. More specifically, rRNA sequence information was obtained by first using oligonucleotide primers complementary to conserved regions which vary little between prokaryotic organisms. The oligonucleotide primers were hybridized to the conserved regions in purified rRNA which were specific to the 28S subunit, and extended with the enzyme reverse transcriptase and deoxyribonucleotides to produce cDNA. E. g., Lane et al., *Proc. Nat'l Acad. Sci. USA* 82:6955 (1985).

B. Probe Design

Strands of deoxyribo- ("DNA") or ribo- ("RNA") nucleic acid are formed from nucleotide units joined in a specific arrangement, or sequence. A nucleotide subunit contains a "base" structure and is distinguished from another nucleotide by the base. Bases include adenine (A), cytosine (C), thymine (T), guanine (G), uracil (U), or inosine (I)).

The structures of the bases in the nucleotides permit certain pairs of bases to interact with one another through the formation of hydrogen bonds. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs. Bases which can hydrogen bond are said to be complementary to one another.

Two single strands of DNA or RNA may specifically align and associate ("hybridize") to form a double stranded-structure in which the two strands are held together by the hydrogen bonds which form between pairs of complementary bases. When a first single-strand of nucleic acid contains sufficient contiguous complementary bases to a second, and those two strands are brought together under conditions promoting their hybridization, double-stranded nucleic acid results. Under appropriate conditions, double-stranded DNA/DNA, RNA/DNA, or RNA/RNA hybrids may be formed. Conditions which decrease the likelihood of forming a given double-stranded hybrid are said to be more stringent conditions than conditions in which hybrid formation is less likely.

A probe is generally a single-stranded nucleic acid sequence which is complementary to some degree to a nucleic acid oligonucleotide "target region" consisting of a "target sequence" sought to be detected. The probe may contain a detectable moiety such as a radioisotope, antigen or chemiluminescent moiety. A background description of the use of nucleic acid hybridization as a procedure for the detection of particular nucleic acid sequences is described by Hogan et al., International Patent Application No. PCT/US87/03009, entitled "Nucleic Acid Probes for Detection and/Or Quantitation of Non-Viral Organisms," hereby incorporated by reference herein.

Using methods known to those skilled in the art, and described herein, variable regions of rRNA sequences from the 28S rRNA of *Coccidioides immitis* were identified. The rRNA molecule exhibits a close relationship of secondary structure to function. This close relationship is caused in part by intramolecular hydrogen bonding interactions between different regions of the rRNA molecule. The hydrogen bond interactions leads to the formation of a double helix structure whose "strands" are different regions of the same rRNA molecule. The formation of this double-stranded helix imposes restrictions on evolutionary changes in the primary sequence so that the secondary structure is maintained. This allows two very different sequences to be aligned based on the conserved primary sequence and also on the conserved secondary structure elements. Potential target sequences for the hybridization assay probes described herein were identified by noting variations in the homology of the aligned sequences.

The sequence evolution at each of the variable regions is mostly divergent. Because of this divergence, corresponding rRNA variable regions of more distant phylogenetic relatives of *Coccidioides immitis* show greater differences from *Coccidioides immitis* rRNA than do the rRNAs of phylogenetically closer relatives. Sufficient variation between *Coccidioides immitis* and its clinically important, closely related phylogenetic relatives, such as *Blastomyces dermatitidis* and *Histoplasma capsulatum*, was observed to identify preferred target sites and design hybridization assay probes useful for distinguishing between nucleic acids of these organisms. These variable regions were subsequently used as target sequence regions for hybridization assay probes.

B. Oligonucleotide Probes

The present application describes hybridization use in a specific assay to detect *Coccidioides immitis*, distinguishing it from closely related taxonomic or phylogenetic neighbors. Also described are amplification oligonucleotides which can be used to amplify target sequences and helper probes to facilitate probe:target hybrid formation.

A hybridization assay probe is an oligonucleotide which can distinguish *Coccidioides immitis* from closely related phylogenetic neighbors, by preferentially hybridizing to a *Coccidioides immitis* target nucleic acid sequence region under stringent hybridization assay conditions. The featured probes consist of one of the following sequences: SEQ ID NOs:21–24.

By "oligonucleotide," "nucleotide polymer" or "nucleic acid" is meant two or more nucleotide subunits covalently joined together. The sugar groups of the nucleotide subunits may be ribose, deoxyribose, or modified derivatives thereof such as O-methyl ribose. The nucleotide subunits may be joined by linkages such as phosphodiester linkages, modified linkages or by nonnucleotide moieties, that do not prevent preferential hybridization of the oligonucleotide to its complementary target nucleic acid. Modified linkages include those linkages in which a standard phosphodiester linkage is replaced with a different linkage, such as a phosphothionate linkage, or methylphosphonate linkage.

The probes are isolated nucleic acids. By "isolated nucleic acid" is meant an oligonucleotide or nucleic acid molecule which is present in a form not found in nature without human intervention (e.g., recombined with foreign nucleic acid, isolated, or purified to some extent). Preferably, the isolated nucleic acid probe is present in a preparation where it constitutes at least 90% of the total nucleic acid present prior to its use.

The probes may also contain additional nucleotides complementary, or not complementary, to nucleic acid sequences contiguous to the target region, so long as such additional nucleotides do not prevent hybridization to the target region, and in the case of hybridization assay probes do not prevent preferential hybridization. Non-complementary sequences, such as a promoter sequence, a binding site for RNA transcription, a restriction endonuclease recognition site, or sequences which will confer a desired secondary or tertiary structure such as a catalytic active site can be used to facilitate detection and/or amplification.

As illustrated by examples described below, the described hybridization assay probes can detect *Coccidioides immitis* and distinguish it from *Malbranchea dendriticus* and *Oidiodendron echinalatum*. The probes can also distinguish *Coccidioides immitis* from other closely related taxonomic or phylogenetic neighbors, such as *Blastomyces dermatitidis* and *Histoplasma capsulatum*.

C. Hybridization

Hybridization assay probes and helper probes hybridize to their target sequence under stringent hybridization conditions. Oligonucleotides acting as helper probes or amplification oligonucleotides do not need to be able to preferentially hybridize to *Coccidioides immitis* nucleic acid.

Preferential hybridization of hybridization assay probes to their target nucleic acids can be accomplished by choosing the appropriate hybridization assay conditions and proper probe design. The stability of the probe: target nucleic acid hybrid should be chosen to be compatible with the assay and washing conditions so that stable, detectable hybrids form only between nucleic acids having highly complementary sequences. Manipulation of one or more of the different assay parameters determines the exact sensitivity and specificity of a particular hybridization assay probe.

Preferential hybridization can occur under stringent hybridization assay conditions. In general, reducing the degree of complementarity of an oligonucleotide targeted region to its target sequence region decreases the degree or rate of hybridization of the probe oligonucleotide to its target sequence region. However, additional non-complementary nucleotide(s) may facilitate the ability of an oligonucleotide to discriminate against non-target organisms.

Preferential hybridization can be measured using techniques known in the art and described herein, such as in the examples provided below. Preferably, there is at least a 100-fold difference between target and non-target hybridization signals, more preferably at least a 1000-fold difference, even more preferably at least a 10,000-fold difference. Also preferably, non-target hybridization signals are not more than background level.

The following guidelines are useful for designing probes and determining specific stringent hybridization assay conditions. Because the sensitivity and specificity of hybridization reactions such as those described herein are affected by a number of factors, including the hybridization assay probe nucleotide sequence and length, the sequence of the target sequence region, the degree of homology between the target sequence and the analogous ribosomal nucleic acid sequences from closely related organisms, the hybridization temperature, and the composition of hybridization reagents, the manipulation of one or more of those factors will determine the exact sensitivity and specificity of a particular probe, whether perfectly complementary to its target or not. The importance and effect of various hybridization assay conditions, explained further herein, are known to those skilled in the art.

First, the stability of the probe:target nucleic acid hybrid should be chosen to be compatible with the assay and washing conditions so that stable, detectable hybrids form only between nucleic acids having highly complementary sequences. Probes should be designed to have an appropriate melting temperature (Tm). This may be accomplished by varying the probe length and nucleotide composition (percentage of G+C versus A+T). The probe length and nucleotide composition are preferably chosen to correspond to a Tm about 2°–10° C. higher than the temperature at which the final assay will be performed. For instance, the Tm can be increased by avoiding long A and T rich sequences, or by terminating the hybrids with G:C base pairs. The beginning and end points of the probe should be chosen so that the length and % G and % C result in a Tm about 2°–10° C. higher than the temperature at which the final assay will be performed.

In general, the optimal hybridization temperature for an oligonucleotide is approximately 5° C. below the melting temperature for a given duplex. Incubation at temperatures below the optimum temperature may allow mismatched base sequences to hybridize and can therefore decrease specificity. The longer the oligonucleotide, the more base pairs are present to hydrogen bond and, in general, the higher the Tm. The base composition of the probe is significant because G-C base pairs exhibit greater additional hydrogen bonding and therefore greater thermal stability than A-T base pairs. (See, e.g., 2 Sambrook, et al., Molecular Cloning: A Laboratory Manual 11 (2d ed. 1989) [hereinafter *Molecular Cloning*].) Thus, hybridization involving complementary nucleic acids of higher G-C content will be stable at higher temperatures.

To ensure specificity of a hybridization assay probe for its target, it is preferable to design probes which hybridize only with target nucleic acid under conditions of high stringency. Under high stringency conditions only highly complementary nucleic acid hybrids will form. Accordingly, the stringency of the assay conditions determines the amount of complementarity which should exist between two nucleic acid strands in order to form a hybrid under those conditions. Stringency should be chosen to maximize the difference in stability between the probe:target hybrid and potential probe:non-target hybrids.

In addition, proper specificity may be achieved by minimizing the length of the hybridization assay probe having perfect complementarity to sequences of non-target organisms by minimizing the length of perfect complementarity to non-target organisms, avoiding G and C rich regions of homology to non-target sequences, and by constructing the probe to contain as many destabilizing mismatches to non-target sequences as possible. Whether a probe sequence is appropriate for detecting only a specific type of organism depends largely on the thermal stability difference between probe: target hybrids and probe:non-target hybrids. In designing probes, the differences in these Tm values should be as large as possible (e.g., at least 2° C. and preferably 5° C. or more).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs from it merely by a single base. While it is possible for nucleic acids that are not perfectly complementary to hybridize, the longest stretch of perfectly homologous base sequence generally determines hybrid stability.

Third, regions of the rRNA which are known to form strong internal structures inhibitory to hybridization are less preferred target regions. Likewise, probes with extensive self-complementarity should be avoided. If a strand is wholly or partially involved in an intramolecular or intermolecular hybrid it will be less able to participate in the formation of a new intermolecular probe:target hybrid. Ribosomal RNA molecules are known to form very stable intramolecular helices and secondary structures by hydrogen bonding. By designing a probe to a region of the target nucleic acid which remains substantially single-stranded under hybridization conditions, the rate and extent of hybridization between probe and target may be increased.

*Coccidioides immitis* target sequences may initially be present as part of a nucleic acid duplex. For example, a genomic rDNA target occurs naturally in a double-stranded form. The polymerase chain reaction (PCR) also gives rise to a double-stranded product. These double-stranded targets require denaturation prior to hybridization. Appropriate denaturation and hybridization conditions are known in the art (e.g., E. M. Southern, *J. Mol. Biol.* 98:503 (1975)).

The rate of hybridization may be measured by determining the $C_0T_{1/2}$. The rate at which a probe hybridizes to its target is a measure of the thermal stability of the target secondary structure in the probe region. The standard measurement of hybridization rate is the $C_0T_{1/2}$ which is measured as moles of nucleotide per liter times seconds. Thus, it is the concentration of probe times the half-life of hybridization at that concentration. This value is determined by hybridizing various amounts of probe to a constant amount of hybrid for a fixed time.

For example, 0.05 pmol of target is incubated with 0.0012, 0.025, 0.05, 0.1 and 0.2 pmol of probe for 30 minutes. The amount of hybrid after 30 minutes is measured by the Hybridization Protection Assay as described below. The signal is then plotted as a log of the percent of maximum Relative Light Units (RLU) (from the highest probe concentration) versus probe concentration (moles of nucleotide per liter). RLU are a measurement of the quantity of photons emitted by the labeled-probe measured by the luminometer. The $C_0T_{1/2}$ is found graphically from the concentration corresponding to 50% of maximum hybridization multiplied by the hybridization time in seconds. These values range from $9.0\times10^{-6}$ to $9\times10^{-5}$ with the preferred values being less than $3.5\times10^{-5}$.

Other methods of nucleic acid reassociation can be used. For example, Kohne and Kacian, EP 229442, entitled "Accelerated Nucleic Acid Reassociation Method," describes a method to accelerate nucleic acid reassociation.

A preferred method to determine Tm measures hybridization using a hybridization protection assay (HPA) according to Arnold, et al., U.S. Pat. No. 5,283,171, entitled "Homogeneous Protection Assay." Tm can be measured using HPA in the following manner. Probe molecules are labeled with an acridinium ester. Probe:target hybrids are formed in a lithium succinate buffer (0.1M lithium succinate buffer, pH 5.0, 2 mM EDTA, 2 mM EGTA, 10% (w/v) lithium lauryl sulfate) using an excess amount of target. Aliquots of the solution containing the nucleic acid hybrids are then diluted in the lithium succinate buffered solution and incubated for five minutes at various temperatures starting below that of the anticipated Tm (typically 55° C.) and increasing in 2°–5° increments. This solution is then diluted with a mild alkaline borate buffer (0.15M sodium tetraborate, pH 7.6, 5% (v/v) TRITON® X-100) and incubated at a lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer (e.g., the Gen-Probe LEADER® I or LEADER ®50). The resulting data is plotted as percent of maximum signal (usually from the lowest temperature) versus temperature. The Tm is defined as the temperature at which 50% of the maximum signal remains. In addition to the method above, Tm may be determined by isotopic methods known to those skilled in the art (see e.g., Hogan et al., supra).

The Tm for a given hybrid varies depending on the nature of the hybridization solution used. Factors such as the concentration of salts, detergents, and other solutes can affect hybrid stability during thermal denaturation (see J. Sambrook, et al., supra). Conditions such as ionic strength and incubation temperature under which a probe will be used should be taken into account in constructing a probe. It is known that the thermal stability of a hybrid nucleic acid increases with the ionic strength of the reaction mixture. On the other hand, the addition of chemical reagents which disrupt hydrogen bonds, such as formamide, urea, DMSO and alcohols, can greatly reduce hybrid thermal stability and thereby increase the stringency of hybridization. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

Examples of specific stringent hybridization conditions for hybridization assay probes are provided in the examples described below. Additional sets of stringent hybridization conditions can be determined based on the present disclosure by those of ordinary skill in the art.

D. Oligonucleotide Synthesis

Defined oligonucleotides may be produced by any of several well known methods, including automated solid-phase chemical synthesis using cyanoethylphosphoramidite precursors. Barone et al., *Nucleic Acids Research* 12:4051 (1984). In addition, other well-known methods for construction of synthetic oligonucleotides may be employed. *Molecular Cloning*, supra (2:11). Following synthesis and purification of an oligonucleotide, several different procedures may be utilized to determine the acceptability of the oligonucleotide in terms of size and purity. Such procedures include polyacrylamide gel electrophoresis and high pressure liquid chromatography, both of which are known to those skilled in the art.

Once synthesized, selected oligonucleotide hybridization assay probes may also be labeled with a reporter group by an of several well known methods. *Molecular Cloning*, supra (2:11). Useful labels include radioisotopes as well as non-radioactive reporting groups. Isotopic labels include $^3H$, $^{35}S$, $^{32}P$, $^{125}I$, Cobalt and $^{14}C$. Isotopic labels can be introduced into an oligonucleotide by techniques known in the art such as nick translation, end labeling, second strand synthesis, reverse transcription, and by chemical methods. When using radio-labeled probes, hybridization can be detected by autoradiography, scintillation counting, or gamma counting. The chosen detection method depends on the hybridization conditions and the particular radio-isotope used for labeling.

Non-isotopic materials can also be used for labeling, and may be introduced internally between nucleotides or at an end of the oligonucleotide. Modified nucleotides may be incorporated enzymatically or chemically. Chemical modifications of the probe may be performed during or after synthesis of the probe, for example, by the use of non-nucleotide linker groups as described by Arnold et al., entitled "Non-Nucleotide Linking Reagents for Nucleotide Probes," EPO application number 88308766.0, publication number 313219 [hereinafter *Non-Nucleotide Linking Reagents*], hereby incorporated by reference herein. Non-isotopic labels include fluorescent molecules, chemiluminescent molecules, enzymes, cofactors, enzyme substrates, haptens or other ligands.

Preferably, the hybridization assay probes are labeled with an acridinium ester. Acridinium ester labeling may be performed as described by Arnold et al., U.S. Pat. No. 5,185,439 entitled "Acridinium Ester Labeling and Purification of Nucleotide Probes" issued Feb. 9, 1993 and hereby incorporated by reference herein.

II. Hybrids Containing a Hybridization Assay Probe and a *Coccidioides Immitis* Target Sequence.

Another aspect of this invention is a hybrid formed by a hybridization assay probe and a target sequence from *Coccidioides immitis*. The formed hybrid is useful for detecting the presence of target. For example, acridinium ester ("AE") present in hybrid is resistant to hydrolysis in alkali solution while acridinium ester present in single-stranded nucleic acid is hydrolyzed in alkali solution. Thus, binding of AE-labeled probe to target can be detected, after hydrolysis of the unbound AE-labeled probe, by measuring chemiluminescence of acridinium ester remaining in the nucleic acid hybrid. Additionally, the formed hybrid can be used to purify hybridized target from unhybridized probe, thereby removing background due to unhybridized probe. For example, hybrid molecules can be selectively retained on hydroxyapatite columns or filters using methods well known to those skilled in the art.

III. Mixes of Hybridization Assay Probes and Helper Probes

Mixes of hybridization assay probes and helper probes can be used in the detection of *Coccidioides immitis*. Helper probes are used to enhance the rate of nucleic acid hybridization of an assay probe with its target nucleic acid and to facilitate the hybridization of the hybridization assay probe to its target. In addition, helper probes are sufficiently complementary to their target nucleic acid sequence to form a helper probe:target duplex under stringent hybridization assay conditions. The stringent hybridization assay conditions used with a given helper probe are determined by the conditions in which a hybridization assay probe is used to preferentially hybridize to its target sequence.

Regions of single-stranded RNA and DNA can be involved in secondary and tertiary structures even under stringent hybridization assay conditions. Such structures can sterically inhibit, or even block hybridization of a hybridization assay probe to its target region. Hybridization of the helper probe alters the secondary and tertiary structure of the target nucleic acid, thereby rendering the hybridization assay probe target region more accessible. As a result helper probes enhance the kinetics and/or the Tm of the target:hybridization probe duplex. Helper probes are generally selected to hybridize to nucleic acid sequences located near the hybridization assay probe target region.

Helper probes which can be used with the hybridization assay probes of the present invention are targeted to target nucleic acid sequence regions of the sequence provided by SEQ ID No: 26. The targeted region in the helper probe which is complementary to the target region preferably contains at least 10 nucleotides of which at least 9 out of the 10 nucleotides are perfectly complementary to a nucleic acid sequence present in the target region.

V. Amplification Oligonucleotides and Amplification Assay Conditions

Methods of amplifying the number of target sequences in a sample can be combined with the use of probe sequences to increase the sensitivity and applicability of the detection assay. (Miller, et al., Evaluation of Gen-Probe Amplified Mycobacterium Tuberculosis Direct Test and PCR for Direct Detection of *Mycobacterium tuberculosis* in Clinical Specimens, J. Clin. Micro. 1994: 393–397; Reddy, et al., Specific amplification of *Aspergillus fumigatus* DNA by polymerase chain reaction, Mol. Cell. Probes 7: 121–126 (1993)).

Amplification oligonucleotides can act as primers for primer extension reactions and may also be part of promoter-primer combinations to amplify a *Coccidioides immitis* target sequence by TMA. Preferably the amplification oligonucleotide will contain a primer sequence having, consisting essentially of, consisting of, or substantially similar to a sequence provided by SEQ ID NOs: 29, 31, 33, 35, 37, 39. More preferably, the amplification oligonucleotide will contain a primer sequence having, consisting essentially of, consisting of, or substantially similar to a sequence provided by SEQ ID NO: 33, 35, 37, 39. Even more preferably, the amplification oligonucleotide will contain a primer sequence having, consisting essentially of, consisting of, or substantially similar to a sequence provided by SEQ ID NO: 37, 39. Preferably the amplification oligonucleotide containing a primer sequence will have a promoter sequence attached to the 5' terminus of the primer sequence. Preferably the promoter sequence will have, consist essentially of, consist of, or be substantially similar to SEQ ID NO: 41.

Preferably the amplification oligonucleotides for use in TMA have, consist essentially of, consist of, or are substantially similar to a sequence corresponding to SEQ ID NOs: SEQ ID NOs:1, 5, 13. More preferably, the amplification oligonucleotide will have, consist essentially of, consist of, or be substantially similar to a sequence corresponding to SEQ ID NOs: 5, 13. In an even more preferred embodiment, the amplification oligonucleotide will have, consist essentially of, consist of, or be substantially similar to a sequence corresponding to SEQ ID NO: 13.

The degree of amplification observed with a set of primers or promoter-primers depends on several factors, including the ability of the oligonucleotides to hybridize to their specific target sequences and their ability to be extended or recognized by an RNA polymerase. While oligonucleotides of different lengths and base composition may be used, more preferred amplification oligonucleotides have target binding regions of 30–60 bases and a predicted hybrid Tm of about 65° C.

A target nucleic acid sequence present on a nucleic acid molecule can be amplified using a primer amplification oligonucleotide which hybridizes to the anti-sense target strand 3' of the target sequence and a promoter-primer amplification oligonucleotide which hybridizes to the sense strand 3' of the target sequence. Extension of the promoter-primer gives rise to RNA copies of the target sequence. Extension of the primer on the anti-sense strand gives rise to copies of the sense strand "template" for the RNA polymerase which recognizes the promoter-primer. Preferably primers have, consist essentially of, consist of, or are substantially similar to the sequences provided by SEQ ID NOs: 9, 11. These primers may also contain an additional promoter sequence added to the 5' terminus of the primer sequence.

The preferred target sites for amplification oligonucleotides are regions greater than about 15 bases in length. The amplified region, defined by the amplification oligonucleotides, is preferably about 350 bases, and more preferably within 150 bases.

Parameters affecting probe hybridization such as Tm, complementarity and secondary structure also affect primer hybridization and therefore performance of the amplification oligonucleotides. These considerations, which were discussed above in the section concerning probe design, can be modified depending upon the amplification conditions. For example, amplification can be carried out under conditions of lower stringency than diagnostic hybridization assay conditions.

The degree of non-specific extension (primer-dimer or non-target copying) can affect amplification efficiency. Primers are preferably selected to have low self-or cross complementarity, particularly at the 3' ends of the sequence. Long homopolymer tracts and high GC content are preferably avoided to reduce spurious primer extension. Computer programs are commercially available to aid in this aspect of the design.

Probe mixes containing hybridization assay probes, helper probes, and amplification oligonucleotides can also be used in amplification assays for the detection of *Coccidioides immitis*.

IV. EXAMPLES

Examples are provided below illustrating different aspects and embodiments of the present invention. The examples illustrate methodologies by which oligonucleotides described herein can be obtained and tested.

Example I

Procedures

Example A

Lysis of Fungal Strains and Clinical Specimens.

Reference fungal strains (Table 1) used in the nucleic acid amplification experiments were obtained from the American Type Culture Collection (ATCC, Rockville, Md.) and cultured on Sabourd's dextrose agar. Clinical specimens were cultured and the fungi were identified using standard culture and identification methods. In addition, fungal colonies were identified as *Coccidioides immitis* using the AccuProbe® *Coccidioides immitis* Culture Identification Test.

Sputum specimens were digested by treating with an equal volume of N-acetyl-L-cysteine-NaOH (1%) for 15 minutes. 1.5 mL aliquots were concentrated by centrifugation at 10,000×g for 5 min. Kent, P. T., Kubica G. *Public Health Mycobacteriology. A Guide for the Level III Laboratory*. Atlanta, Ga.; Centers for Disease Control (1985). Supernatant fluid was decanted, and 50 µl of sediment was added to a TB lysing tube containing 0.17 g of 0.2–0.3 mm glass beads, 110 µl 5% w/v sorbitol, and 300 µl of a solution of 10 mM N-acetyl-L-cysteine-NaOH, 40 mM Trizma base, 2 mM disodium EDTA adjusted to pH 8.0 with HCl (TB SDB solution).

100 µl of fluid of upper chest fluid, lower chest fluid, expressed swabs or abscess fluid was added to 1 ml of flashtrack wash solution (18 mM NaCl, 5.7 mM sodium azide, 5 mM HEPES (0.5 sodium salt), 0.1% w/v Saponin, adjusted to pH 7.5 with 4M NaOH). Samples were vortexed and then centrifuged in eppendorf tubes for 5 min. at 10,000 g. The supernatants were decanted and resuspended in 1 ml of flashtrack wash solution. The pellet was resuspended in 200 µl TB SDB and vortexed. 50 µl of each sample was added to a TB lysing tube containing 0.17 g of 0.2–0.3 mm glass beads, 110 µl 5% w/v sorbitol, and 300 µl of TB SDB and glass beads.

Fluid specimens such as cerebrospinal fluid (CSF) were concentrated by centrifugation in the same manner, the supernatant decanted, and 50 µl of sediment was added to a TB lysing tube containing 0.17 g of 0.2–0.3 mm glass beads, 110 µl 5% w/v sorbitol, and 300 µl of TB SDB.

For measurement from cultures, 1 µl loopful of fungal cells were added to a TB lysing tube containing 0.17 g of 0.2–0.3 mm glass beads, 110 µl 5% w/v sorbitol, and 300 µl of TB SDB.

Once samples were added to the TB lysing tube, samples from sputum and other fluids were treated in the same manner. The samples were sonicated in a waterbath for 15 minutes at room temperature. Next the cells were heatkilled in a heat block for 10 min. at 95° C. Dilutions were then made in TB SDB. Samples were used promptly or frozen at –70° C. for later use.

Example B

Amplified Assay for *Coccidioides immitis*.

The assay illustrated in this section utilizes an isothermal target-based, transcription mediated amplification (TMA) system. Following lysis of the fungal organisms by sonication in an enclosed tube using a water bath sonicator, the released rRNA was amplified via the TMA method described below into numerous target sequences which were then detected in the same tube using a homogenous protection assay.

Liquid primers were diluted 30 pmols each/25 µl of a solution of PAR (4 mM ATP, 4 mM CTP, 4 mM GTP, 4 mM UTP, 1 mM dATP, 1 mM dCTP, 1 mM dGTP, 1 mM dTTP, 40 mM Trizma Base, 20 mM $MgCl_2$, 17 mM KCl, 5% w/v polyvinylpyrrolidone, adjusted to pH 7.5 using 1M NaOH and 6M HCl). 25 µl of the primers in PAR were added to the bottom of a polypropylene test tube. 200 µl of the oil reagent were added to each tube. 50 µl of rRNA diluted to the correct concentration in TB SDB were added to each tube (except for the negative controls which received 50 µl of SDB only). Samples were then placed in a heat block at 95° C. for 10 min. The tubes were placed in a water bath at 42° C. for 5 min. 25 µl containing reverse transcriptase (458 units/µl and T7 RNA polymerase (367 units/µl) in enzyme dilution buffer (60 mM N-acetyl-L- cysteine, 1 mM EDTA (free acid), 0.01% Phenol Red (0.5% solution), 140 mM Trizma Base, 70 mM KCl, 20% v/v glycerol, and 10% v/v Triton X-102 adjusted to pH 8 with 6M HCl) was added to each tube while the tubes remained in the 42° C. water bath. The rack was gently shaken, the tubes were covered with sealing cards, and the tubes were incubated at 42° C. for an additional 2 hours. The tubes were removed from the water bath, and the hybridization probe assay was performed. Alternatively, samples could be refrigerated for later testing.

Two primers were used in the amplification step: a T7 RNA polymerase promoter/primer, and a primer. The T7 promoter-primer was complementary to a region of the sense strand 3' of the hybridization probe target sequence. Extension of this primer gives rise to RNA copies of the target sequence.

The primer is complementary to a region of the anti-sense strand 3' from the target sequence. Extension of the primer on the anti-sense strand therefore gives rise to copies of the sense strand "template" for the T7 RNA polymerase. Amplification of antisense target sequences by TMA thus occurred as the sense strand was first copied by the DNA polymerase activity of reverse transcriprase and second, these sense strand copies were used as templates by RNA polymerase to amplify the anti-sense strand nucleic acids containing the target sequence. The process repeats autocatalytically. Amplification of rRNA from clinical specimens is also described in Jonas et al., *Detection and Identification of Mycobacterium tuberculosis Directly from Sputum Sediments by Amplification of rRNA*, pp. 2410–2416 (1993).

Example II

Hybridization Probe Assay:

A probe specific for *Coccidioides immitis* was identified by sequencing with a primer complementary to the 28S rRNA of *Coccidioides immitis*. The probe SEQ ID NO:21 was characterized and shown to be specific for *Coccidioides immitis*. The probe distinguished *Coccidioides immitis* from phylogenetically near, clinically important neighbors including *Blastomyces dermatitidis* and *Histoplasma capsulatum*.

To demonstrate the reactivity and specificity of the probe for *Coccidioides immitis*, a hybridization probe assay was performed. RNA was hybridized to the acridinium ester-labeled probe in the presence of unlabeled helper probe. Helper probe consisted of the sequence corresponding to SEQ ID N0:25: GAACAGGACG TCATAGAGGG TGAGAATCC.

Ninety µl of a probe mixture in probe hybridization buffer (100 mM succinic acid, 230 mM of LiOH, 150 mM aldrithiol-2, 1.2M $LiCl_2$, 20 mM EDTA, 20 mM EGTA, 3% v/v ethyl alcohol, 2% v/v lithium lauryl sulfate adjusted to pH 4.7 with 2M LiOH) containing 2.5 pmols helper probe and 10 μl of probe (0.05 or 0.1 pmols/reaction) were added to each tube. The probe mixture contained an acridinium ester-labeled probes having one of the following nucleotide sequences:

(SEQ ID NO:17) GCAGCCACGG CATAAGTTCC TTG (SEQ ID NO:21) GCGCCACGGC ATAAGTTCCT TG and unlabeled helper probe:

(SEQ ID N0:25) GAACAGGACG TCATAGAGGG TGAGAATCC.

The tubes were vortexed well and incubated at 60° C. for 15 min. 300 μl of 600 mM boric acid, 182 mM NaOH, and 1% v/v adjusted to pH 8.5 with 4M NaOH (selection reagent) was added to each sample. The samples were then incubated at 60° C. for 10 min. The samples were removed from the water bath and allowed to stand at room temperature for 5 min. before reading in a Gen-Probe luminometer for 2 seconds with a standard 2 injection format. A value of 30,000 relative light units (RLU) was used as the proposed cutoff for a positive test. Each run included amplification positive and negative controls. Quadruplicate assays were run for each determination, and the mean RLU values were calculated.

Example IV

Specificity of the Amplified Hybridization Probe Assay.

Purified rRNA preparations and sonicated fungal culture lysates were used to estimate the specificity of the test. Two probes were tested in the amplification assay: SEQ ID NO: 17 (Tables 1A-C) and SEQ ID NO: 21 (Table 1D-E). A T7 promoter-primer containing the sequence corresponding to SEQ ID NO:13 and a primer containing the sequence provided by SEQ ID NO:9 were used to obtain the results in Tables 1A and 1C. A T7 promoter-primer containing the sequence corresponding to SEQ ID NO:5 and a primer sequence containing the sequence provided by SEQ ID NO:9 were used to obtain the results in Table 1B. Strains representing other single pathogens and closely related organisms were included in the panel. Only *Coccidioides immitis* strains were positive (>30,000 RLU) in the assay.

The following data show that the probes did not cross react with organisms from a wide phylogenetic cross section. The samples were also tested with a probe which has a very broad specificity. A positive signal from this probe provided confirmation of sample adequacy (data not shown).

TABLE IA

Specificity of Hybridization Probe SEQ ID NO:17 With rRNA Templates

| ATCC Organism | rRNA Concentration | Average RLU's |
|---|---|---|
| (–) Control | 0 fg | 1,615 |
| *Coccidioides immitis* (+) cont | 500 fg | 391,321 |
| *Malbranchea albolutea* | 500 fg | 1,264 |
| *Blastomyces dermatitidis* | 500 fg | 1,247 |
| *Histoplasma capsulatum* | 500 fg | 1,171 |
| *Auxarthron thaxteri* | 500 fg | 4,613 |
| *Gymnoascus dugwayensis* | 500 fg | 1,255 |
| (–) cont | 0 fg | 5,867 |
| *Coccidioides immitis* (+) cont | 50 fg | 450,393 |
| *Coccidioides immitis* (+) cont | 500 fg | 737,434 |
| *Aspergillus flavus* | 500 fg | 2,432 |
| *Myxotrichum deflexum* | 500 fg | 1,610 |
| *Aspergillus niger* | 500 fg | 2,307 |
| *Candida krusei* | 500 fg | 1,793 |
| *Candida glabrata* | 500 fg | 5,022 |
| *Aspergillus fumigatus* | 500 fg | 2,574 |

TABLE IA-continued

Specificity of Hybridization Probe SEQ ID NO:17 With rRNA Templates

| ATCC Organism | rRNA Concentration | Average RLU's |
|---|---|---|
| *Arachnioites flavoluteus* | 500 fg | 2,929 |
| *Candida parapsilosis* | 500 fg | 2,100 |
| *Oidiodendron echinulatum* | 500 fg | 1,247 |
| *Candida albicans* | 500 fg | 3,189 |

*The RLU's are averages of 4 replicates except for the value for *Candida glabrata* which is the average of 2 replicates. The primers used were the T7 promoter-primer SEQ ID NO:13 and the primer SEQ ID NO:9.

TABLE IB

Specificity of Hybridization Probe (SEQ ID NO:17) With rRNA Templates

| ATCC Organism | rRNA Concentration | Average RLU's |
|---|---|---|
| (–) cont | 0 fg | 2,977 |
| *Coccidioides immitis* (+) cont | 500 fg | 604,535 |
| *Malbranchea albolutea* | 500 fg | 1,247 |
| *Blastomyces dermatitidis* | 500 fg | 2,224 |
| *Histoplasma capsulatum* | 500 fg | 968 |
| *Auxarthron thaxteri* | 500 fg | 1,072 |
| *Gymnoascus dugwayensis* | 500 fg | 7,638 |
| (–) cont | 0 fg | 2,421 |
| *Coccidioides immitis* (+) cont | 50 fg | 618,916 |
| *Coccidioides immitis* (+) cont | 500 fg | 652,483 |
| *Aspergillus flavus* | 500 fg | 2,475 |
| *Myxotrichum deflexus* | 500 fg | 1,572 |
| *Aspergillus niger* | 500 fg | 1,575 |
| *Candida krusei* | 500 fg | 1,702 |
| *Candida glabrata* | 500 fg | 2,234 |
| *Candida albicans* | 500 fg | 1,607 |
| *Arachnioites flavoluteus* | 500 fg | 1,521 |
| *Aspergillus fumigatus* | 500 fg | 2,945 |
| *Candida parapsilosis* | 500 fg | 2,210 |
| *Oidiodendron echinulatum* | 500 fg | 5,726 |

*The RLU's are the averages of 4 replicates except for *Aspergillus flavus*, *Candida krusei* and *Candida galbrata* which are the average of 3 replicates. The T7 promoter/primer which was used contained the sequence provided by SEQ ID NO:5 and the primer which was used contained the sequence in SEQ ID NO:9.

TABLE 1C

Specificity Testing with ATCC Cell Lysates and rRNA*

| Organism | ATCC#** | Average RLU |
|---|---|---|
| *Coccidioides immitis* | 46900 | 1,544,446 |
| *Coccidioides immitis* | 38149 | 1,496,889 |
| *Coccidioides immitis* | 28868 | 1,424,771 |
| *Coccidioides immitis* | 38146 | 1,478,833 |
| *Coccidioides immitis* (1 × 10–2) | 38146 | 1,612,038 |
| *Coccidioides immitis* (1 × 10–5) | 38146 | 1,395,387 |
| *Coccidioides immitis* (1 × 10–9) | 38146 | 810,204 |
| *Histoplasma capsulatum* | 11407 | 968 |
| *Histoplasma capsulatum* | 38904 | 1,110 |
| *Blastomyces dermatitidis* | 60916 | 1,483 |
| *Trichophyton terrestre* | 28188 | 2,865 |
| *Trichophyton rubrum* | 10218 | 4,978 |
| *Trichophyton rubrum* | 28188 | 2,865 |
| *Trichophyton rubrum* | CI-4373 | 3,369 |
| *Uncinocarpus reeseii* | 34533 | 1,891 |
| *Gymnoascus dugwayensis* | 18899 | 1,621 |
| *Arachnioitus flavoluteus* | 28364 | 10,336 |
| | 28364 | 1,903 |
| *Malbranchea dendritica* | 34527 | 4,747 |
| *Malbranchea arcuata* | 34523 | 1,500 |
| *Malbranchea albolutea* | 34522 | 1,871 |

TABLE 1C-continued

| Specificity Testing with ATCC Cell Lysates and rRNA* | | |
|---|---|---|
| Organism | ATCC#** | Average RLU |
| *Malbranchea gypseum* | 24102 | 4,338 |
| *Myxotrichum deflexum* | 15686 | 2,143 |
| *Auxarthron thaxteri* | 15598 | 1,414 |
| *Oidiodendron echinulatum* | 16287 | 1,497 |
| *Aspergillus flavus* | 10124 | 2,432 |
| *Aspergillus niger* | 16888 | 2,307 |
| *Aspergillus fumigatus* | 16907 | 2,574 |
| *Candida krusei* | 6258 | 1,793 |
| *Candida glabrata* | 48435 | 2,234 |
| *Candida albicans* | 18804 | 3,189 |
| *Candida parapsilosis* | 22019 | 2,100 |
| Negative control | | 1,364 |
| *Coccidioides immitis* (+) control | CI-W95 | 1,501,719 |
| *Trichophyton terrestre* | CI-1441 | 1,859 |
| *Trichophyton terrestre* | CI-TR-9 | 2,839 |
| *Trichophyton terrestre* | CI-TR-73 | 2,924 |

*These assays were carried out using a T7 promoter-primer containing the sequence provided by SEQ ID NO:13, an amplification primer containing the sequence provided by SEQ ID NO:9, and the hybridization assay probe containing the sequence provided by SEQ ID NO:17.

**For some organisms, the clinical isolate (CI) number is provided instead of the ATCC number.

TABLE ID

| Specificity of Hybridization Probe SEQ ID NO:21 With rRNA Templates* | | |
|---|---|---|
| ATCC Organism | rRNA Concentration | Average RLU's |
| (-) Control | 0 fg | 938 |
| *Coccidioides immitis* "A" Endospore | $9 \times 10^5$ | 590,111 |
| *Coccidioides immitis* "A" Endospore | $9 \times 10^3$ | 454,899 |
| *Coccidioides immitis* "A" Endospore | 9 | 540,528 |
| *Coccidioides immitis* "A" Endospore | 0.9 | 348,205 |
| *Malbranchea dendritica* | 500 fg | 1,264 |
| *Oidiodendron echinulatum* | 500 fg | 1,247 |

*The T7 promoter/primer used contained the sequence corresponding to SEQ ID NO:13, and the primer used contained the sequence corresponding to SEQ ID NO:9.

TABLE 1E

| Specificity of Hybridization Probe SEQ ID NO:21 With rRNA Templates* | | |
|---|---|---|
| ATCC Organism | rRNA Concentration | Average RLU's |
| (-) cont | 0 fg | 21,616 |
| *Coccidioides immitis* (+) control | 100 fg | 96.453 |
| *Coccidioides immitis* (+) control | 100 fg | 143,076 |
| *Coccidioides immitis* (+) control | 200 fg | 137,590 |
| *Coccidioides immitis* (+) control | 500 fg | 84,636 |
| *Malbranchea albolutea* | 500 fg | 13,873 |
| *Blastomyces dermatitidis* | 500 fg | 11,802 |
| *Histoplasma capsulatum* | 500 fg | 10,790 |
| *Auxarthron thaxteri* | 500 fg | 13,724 |
| *Gymnoascus dugwayensis* | 500 fg | 10,420 |
| *Myxotrichum deflexum* | 500 fg | 17,156 |
| *Aspergillus niger* | 500 fg | 15,943 |
| *Candida krusei* | 500 fg | 16,861 |
| *Candida glabrata* | 500 fg | 12,515 |
| *Arachnioites flavoluteus* | 500 fg | 13,532 |
| *Candida parapsilosis* | 500 fg | 14,368 |
| *Oidiodendron echinulatum* | 500 fg | 12,656 |
| *Candida albicans* | 500 fg | 13,946 |

*The primers used were the T7 promoter-primer having the sequence provided by SEQ ID NO:13 and the primer having the sequence provided by SEQ ID NO:9.

The above data confirm that the probes described herein are capable of distinguishing *Coccidioides immitis* from its closely related phylogenetic neighbors in amplification assays.

Example V

Sensitivity of the Amplified Hybridization Probe Assay To Detect Cultured *Coccidioides immitis*.

The sensitivity of the assay was determined by testing serial dilutions of purified *Coccidioides immitis* rRNA. The test detected as little as 5 fg of rRNA with an average signal of 1,265,406 RLU, a value above the linear range of the luminometer. Two assays using different probes were carried out. The probes contained the sequences in SEQ ID NO: 17 (Table 2) and SEQ ID NO: 21 (Table 3). Another approach to determine the sensitivity of the assay was to test dilutions of 3 different endospore preparations using two different probes: SEQ ID NO: 21 (Table 4) and SEQ ID NO: 17 (Table 5). The number of endospores in each test was determined by direct counting using a hemocytometer. The amplified assay was able to detect as little as one endospore per test.

To determine if the assay would produce positive RLU signals in clinical specimens, dilutions of endospores were added to 5 culture-negative sputum sediments previously digested according to the method of Kent, et al. Kent, P. T., Kubica G. *Public Health Mycobacteriology. A Guide for the Level III Laboratory*. Atlanta, Ga.; Centers for Disease Control (1985). Again, positive signals were obtained with as few as one endospore per test. Endospores were also seeded into aliquots of culture-negative CSF prior to centrifugation, and as few as 3 endospores per test produced a positive result.

TABLE 2

| Sensitivity of Hybridization Assay Probe SEQ ID NO:17 Using rRNA Template | | |
|---|---|---|
| Amplification Oligonucleotides | *C. immitis* rRNA Concentration | Average RLU's |
| SEQ ID NO:13 & SEQ ID NO:9 | 5 fg | 1,265,406 |
| SEQ ID NO:13 & SEQ ID NO:9 | 20 fg | 1,878,058 |
| SEQ ID NO:13 & SEQ ID NO:9 | 50 fg | 1,645,021 |
| SEQ ID NO:13 & SEQ ID NO:9 | 100 fg | 1,749,740 |
| SEQ ID NO:13 & SEQ ID NO:9 | (-) cont | 2,582 |
| SEQ ID NO:5 & SEQ ID NO:9 | 5 fg | 22,979 |
| SEQ ID NO:5 & SEQ ID NO:9 | 20 fg | 343,184 |
| SEQ ID NO:5 & SEQ ID NO:9 | 50 fg | 489,363 |
| SEQ ID NO:5 & SEQ ID NO:9 | 100 fg | 672,477 |
| SEQ ID NO:5 & SEQ ID NO:9 | (-) cont | 1,867 |
| SEQ ID NO:1 & SEQ ID NO:9 | 5 fg | 11,639 |
| SEQ ID NO:1 & SEQ ID NO:9 | 20 fg | 7,191 |
| SEQ ID NO:1 & SEQ ID NO:9 | 50 fg | 45,217 |
| SEQ ID NO:1 & SEQ ID NO:9 | 100 fg | 185,162 |
| SEQ ID NO:1 & SEQ ID NO:9 | (-) cont | 2,299 |

*The RLU's are averages of 4 replicates.

TABLE 3

Sensitivity of Hybridization Assay Probe SEQ ID NO:17 Using rRNA Templates

| Amplification Oligonucleotides | *C. immitis* rRNA Concentration | Average RLU's |
|---|---|---|
| SEQ ID NO:13 & SEQ ID NO:9 | 5 fg | 528,577 |
| SEQ ID NO:13 & SEQ ID NO:9 | 20 fg | 830,764 |
| SEQ ID NO:13 & SEQ ID NO:9 | 50 fg | 743,241 |
| SEQ ID NO:13 & SEQ ID NO:9 | 100 fg | 780,634 |
| SEQ ID NO:13 & SEQ ID NO:9 | (–) cont | 1,779 |
| SEQ ID NO:5 & SEQ ID NO:9 | 5 fg | 6,517 |
| SEQ ID NO:5 & SEQ ID NO:9 | 20 fg | 30,320 |
| SEQ ID NO:5 & SEQ ID NO:9 | 50 fg | 159,855 |
| SEQ ID NO:5 & SEQ ID NO:9 | 100 fg | 238,620 |
| SEQ ID NO:5 & SEQ ID NO:9 | (–) cont | 1,842 |
| SEQ ID NO:1 & SEQ ID NO:9 | 5 fg | 9,611 |
| SEQ ID NO:1 & SEQ ID NO:9 | 20 fg | 116,592 |
| SEQ ID NO:1 & SEQ ID NO:9 | 50 fg | 139,480 |
| SEQ ID NO:1 & SEQ ID NO:9 | 100 fg | 120,685 |
| SEQ ID NO:1 & SEQ ID NO:9 | (–) cont | 1,658 |

*The RLU's are averages of 4 replicates.

The results in Tables 2 and 3 illustrate the large difference in the level of signal obtained in amplification assays (as measured in RLU's) using the same primer and three different T7 promoter-primers (SEQ ID NO:13, SEQ ID NO:5, and SEQ ID NO:1). The three promoter-primers were targeted near to each other on *Coccidioides immitis* 28S RNA, contained the same promoter sequence, and had similar length primer sequences. The amplification assays using the promoter-primer containing SEQ ID NO:13 gave rise to the highest signals in the different assays. The assays using the promoter-primer containing SEQ ID NO:5 gave rise to higher signals than the assays using the promoter-primer SEQ ID NO:1 when the probe containing SEQ ID NO:17 was used. The amplification assays using the promoter-primer containing SEQ ID NO:5 gave rise to higher signals at 50 fg and 100 fg of rRNA than the amplification assays using the promoter-primer containing SEQ ID NO:1 when the probe containing SEQ ID NO:21 was used.

The sequence specified in SEQ ID NO:13 is 53 nucleotides long and is complementary to a 26 nucleotide region which begins 3 nucleotides 3' of the target region targeted by the sequence SEQ ID NO:21. The sequence provided in SEQ ID NO:5 is 49 nucleotides long and is complementary to a 22 nucleotide region which begins 15 nucleotides 3' of the target region targeted by the sequence SEQ ID NO:21. The sequence provided in SEQ ID NO:1 is 51 nucleotides long and is complementary to a 24 nucleotide region which begins 23 bases 3' of the target region targeted by the SEQ ID NO:21. Thus, the results achieved using the three promoter primers are very different, despite the similarity between the three promoter-primers.

TABLE 4

Sensitivity of Hybridization Assay Probe (SEQ ID NO:21) Using Endospore and Spherule Dilutions*

| Sample Type | Endospore Input | Average RLU's |
|---|---|---|
| "A" Endospore | $9 \times 10^5$ | 590,111 |
| "A" Endospore | $9 \times 10^3$ | 454,899 |
| "A" Endospore | 9 | 540,528 |
| "A" Endospore | 0.9 | 348,205 |
| "B" Endospores | $6.5 \times 10^4$ | 580,569 |
| "B" Endospores | $6.5 \times 10^2$ | 606,883 |
| "B" Endospores | 6.5 | 415,189 |
| "B" Endospores | 0.65 | 143,655 |
| "B" Endospores | 0.065 | 2,289 |
| "C" Mixed Endos & Spherules | $3.25 \times 10^6$ | 573,807 |
| "C" Mixed Endos & Spherules | $3.25 \times 10^4$ | 623,849 |
| "C" Mixed Endos & Spherules | $3.25 \times 10^2$ | 494,017 |
| "C" Mixed Endos & Spherules | 3.25 | 131,760 |
| "C" Mixed Endos & Spherules | 0.325 | 1,679 |
| (–) control | None | 983 |

*The RLU's are averages of 2 replicates. The T7 promoter-primer used contained the sequence provided by SEQ ID NO:13 and the primer used contained the sequence provided by SEQ ID NO:9.

TABLE 5

Sensitivity of Hybridization Assay Probe (SEQ ID NO:17) Using rRNA Templates

| | RLU's |
|---|---|
| "A" Preparation Endospores per Assay | |
| $9 \times 10^5$ | 1619925 |
| $9 \times 10^3$ | 1455427 |
| 9 | 1163369 |
| 0.9 | 360861 |
| "B" Preparation Endospores per Assay | |
| $6.5 \times 10^4$ | 1402927 |
| $6.5 \times 10^2$ | 1347311 |
| 6.5 | 1339671 |
| 0.65 | 533590 |
| 0.065 | 3652 |
| "C" Preparation Mixed Endospores and Spherules | |
| $3.25 \times 10^6$ | 1359644 |
| $3.25 \times 10^4$ | 1366980 |
| $3.25 \times 10^2$ | 1218693 |
| 3.25 | 210010 |
| 0.325 | 2160 |
| Negative Control | 1320 |

*The T7 promoter-primer used contained the sequence corresponding to SEQ ID NO:13 and the primer used contained the sequence provided by SEQ ID NO:9.

Example VI

Sensitivity of the Amplified Hybridization Probe Assay in Detecting *Coccidioides immitis* Directly From Clinical Specimens.

The results (average of 4 replicate RLU values) with clinical specimens are shown in Table 6. Five homogenized lung and pleural tissue specimens from 4 patients gave positive results from 176,235 to 1,475,187 RLU's. Four respiratory secretion specimens (sputum, bronchial washings and chest fluid) from 3 patients gave positive results from 86,998 to 1,342,617 RLU's. One patient with disseminated coccidioidomycosis produced positive signals of 569,969 and 953,985 RLU from swabs of abscess drainage. All of these specimens were positive for *C. immitis* by fungal culture and/or histopathology.

Two CSF specimens and one sputum specimen from three patients were negative by the prototype test. The RLU values ranged from 1,747 to 12,850. These specimens were culture-negative for *C. immitis.*

Additional results confirming the detection of *Coccidioides immitis* in clinical specimens are shown in Tables 7–9. The probe used in these experiments was SEQ ID NO:17. The T7 promoter-primer used contained the sequence corresponding to SEQ ID NO: 13 and the primer used contained the sequence corresponding to SEQ ID NO: 9. *Coccidioides immitis* was detected in pleural tissue, lung abscess tissue, pleural mass, lung mass, lung fluid, a sputum sample, and bronchial wash (Tables 6 and 7). In addition, *Coccidioides immitis* was detected in samples from abscesses (Table 8).

TABLE 6

Patient Specimens

| Patient # | Specimen | Average RLU |
|---|---|---|
| *C. immitis* Culture or Histopathology Positive*: | | |
| 1 | L. Pleural Tissue | 941,285 |
| 1 | L. Pleural Mass | 1,441,898 |
| 2 | L. Lung Abscess | 176,235 |
| 3 | L. Lung Mass | 1,475,187 |
| 4 | R. Lung Fluid | 1,315,485 |
| 5 | Sputum | 1,009,956 |
| 6 | Bronchial Wash | 1,342,617 |
| 7 | Upper Chest Fluid | 258,259 |
| 7 | Lower Chest Fluid | 86,998 |
| 8 | Lateral Leg Abscess | 953,985 |
| 8 | Medial Leg Abscess | 569,969 |
| *C. immitis* Culture Negative Specimens: | | |
| 9 | CSF | 12,850 |
| 10 | CSF | 1,747 |
| 11 | Sputum Sediment | 6,786 |

*The probe used contained the sequence in SEQ ID NO:17. The T7 promoter-primer used contained the sequence provided by SEQ ID NO:13 and the primer used contained the sequence provided by SEQ ID NO:9.

TABLE 7

PATIENT SAMPLES*

| Sample Type | Average rlu's |
|---|---|
| L. Pleural Tissue T40995 | 941,285 |
| T40995 ($10^{-1}$) | 4,043 |
| Lung Abscess Tissue F44901 | 176,235 |
| F44901 ($10^{-1}$) | 294,295 |
| L. Pleural Mass T40996 | 1,441,898 |
| T40996 ($10^{-1}$) | 1,593,774 |
| Left Lung Mass W46404 | 1,475,187 |
| W46404 ($10^{-1}$) | 1,549,916 |
| Right Lung Fluid 94441230212 | 1,315,485 |
| 94441230212 ($10^{-1}$) | 198,645 |
| Sputum Sample PN114 | 1,009,956 |
| PN114 ($10^{-1}$) | 633,191 |
| Bronchial Wash W49281 | 1,342,617 |
| W49281 ($10^{-1}$) | 889,543 |
| (–) Control | 1,052 |
| (+) Control | 1,763,026 |

*The T7 promoter-primer used in these assays contained the sequence provided by SEQ ID NO:13, and the primer used contained the sequence corresponding to SEQ ID NO:9. The probe used contained the sequence provided by SEQ ID NO:17.

TABLE 8

PATIENT SAMPLES*

| Sample Number | Average RLU's |
|---|---|
| L. Pleural Tissue | 5,766 |
| L. Pleural Tissue ($10^{-1}$) | 3,554 |
| L. Pleural Tissue ($10^{-2}$) | 2,832 |
| L. Pleural Tissue ($10^{-3}$) | 2,583 |
| Lung Abscess Tissue | 208,062 |
| Lung Abscess Tissue ($10^{-1}$) | 113,559 |
| Lung Abscess Tissue ($10^{-2}$) | 7,663 |
| Lung Abscess Tissue ($10^{-3}$) | 3,406 |
| L. Pleural Mass | 1,741,846 |
| L. Pleural Mass ($10^{-1}$) | 1,777,578 |
| L. Pleural Mass ($10^{-2}$) | 852,297 |
| L. Pleural Mass ($10^{-3}$) | 265,296 |
| Left Lung Mass | 962,209 |
| Left Lung Mass ($10^{-1}$) | 1,260,207 |
| Left Lung Mass ($10^{-2}$) | 4,592 |
| Left Lung Mass ($10^{-3}$) | 3,920 |
| Right Lung Fluid | 179,199 |
| Right Lung Fluid ($10^{-1}$) | 238,102 |
| Right Lung Fluid ($10^{-2}$) | 8,203 |
| Lung Fluid ($10^{-3}$) | 3,007 |
| Sputum Sample | 816,631 |
| Sputum Sample ($10^{-1}$) | 29,590 |
| Sputum Sample ($10^{-2}$) | 200,518 |
| Sputum Sample ($10^{-3}$) | 2,267 |
| Bronchial Wash | 55,001 |
| Bronchial Wash ($10^{-1}$) | 58,067 |
| Bronchial Wash ($10^{-2}$) | 18,499 |
| Bronchial Wash ($10^{-3}$) | 12,812 |
| (+) Cont | 140,045 |
| (–) Cont | 2,752 |

*The T7 promoter-primer used in these assays contained the sequence provided by SEQ ID NO:13. The primer used contained the sequence corresponding to SEQ ID NO:9. The probe used contained the sequence corresponding to SEQ ID NO:17.

TABLE 9

Patient Samples*

| Sample Type | Average RLU's |
|---|---|
| Elbow Abscess (Garcia) | 1,527,707 |
| Medial Abscess (Garcia) | 1,020,833 |
| Elbow Abscess (Garcia) | 1,178,792 |
| Abscess (Knox) | 1,196,953 |
| Abscess (Knox) | 1,056,303 |
| (–) Cont | 5,007 |

Example VII

Effects of NaOH Concentration on Sensitivity.

In order to determine the effects of NaOH concentration during treatment of sputum specimens with N-acetyl-L-cysteine-NaOH, sputum specimens from two different patients were treated at 1% and 4% NaOH during this step of the sample preparation. The results are shown below in Table 10.

TABLE 10

PATIENT SAMPLES

| TABLE XIV<br>NaOH Concentration | Average RLU's |
|---|---|
| Patient 1: | |
| 1% NaOH | 230,162 |
| 1% NaOH | 203,551 |
| 4% NaOH | 1,005,982 |

TABLE 10-continued

PATIENT SAMPLES

| TABLE XIV NaOH Concentration | Average RLU's |
|---|---|
| 4% NaOH | 1,080,525 |
| Patient 2: | |
| 1% NaOH | 13,875 |
| 1% NaOH | 13,175 |
| 4% NaOH | 157,216 |
| 4% NaOH | 14,530 |
| (–) Control | 5,077 |

Other embodiments are within the following claims. Thus while several embodiments have been shown and described, various modifications may be made, without departing from the spirit and scope of the present invention.

We claim:

1. A nucleic acid hybridization assay probe for detecting *Coccidioides immitis*, comprising a nucleic acid 22–100 nucleotide bases in length comprising a nucleotide base sequence selected from the group consisting of: SEQ ID NO: 21, 22, 23, and 24;

wherein said probe distinguishes *Coccidioides immitis* nucleic acid from *Histoplasma capsulatum* and *Blastomyces dermatitidis* nucleic acid under stringent hybridization assay conditions.

2. The nucleic acid hybridization assay probe of claim 1, wherein said probe contains a detectable label.

3. The nucleic acid hybridization assay probe of claim 1, consisting of said nucleotide base sequence.

4. A nucleic acid hybrid for specific detection of *Coccidioides immitis* comprising:

a nucleic acid hybridization assay probe comprising a nucleic acid 22–100 nucleotide bases in length comprising a nucleotide base sequence selected from the group consisting of: SEQ ID NO: 21, 22, 23, and 24;

and a complementary target sequence of *Coccidioides immitis*, wherein said target sequence is sufficiently complementary to said probe to allow detection of *Coccidioides immitis.*

5. A probe mix comprising:

a nucleic acid hybridization assay probe comprising a 22–100 base pair sequence comprising a nucleotide sequence selected from the group consisting of: SEQ ID NOs: 21, 22, 23, and 24; wherein said probe distinguishes *Coccidioides immitis* nucleic acid from *Histoplasma capsulatum* and *Blastomyces dermatitidis* nucleic acid under stringent hybridization assay conditions, and a helper probe comprising a nucleic acid sequence selected from the group consisting of: SEQ ID NOs: 25, and 27.

6. A method for detecting the presence of *Coccidioides immitis* in a test sample and distinguishing said *Coccidioides immitis* from *Histoplasma capsulatum* and *Blastomyces dermatitidis*, comprising the steps of:

a) contacting said test sample under stringent hybridization assay conditions with a nucleic acid hybridization assay probe which forms a hybrid stable for detection under stringent hybridization conditions with *Coccidioides immitis* nucleic acid, and said probe comprising a nucleic acid 22–100 nucleotide bases in length comprising a nucleotide base sequence selected from the group consisting of: SEQ ID NOs: 21, 22, 23, and 24;

wherein said probe distinguishes *Coccidioides immitis* nucleic acid from *Histoplasma capsulatum* and *Blastomyces dermatitidis* nucleic acid under stringent hybridization assay conditions; and (b) detecting said hybrid as an indication of the presence of *Coccidioides immitis* in said sample.

7. The method of claim 6, further comprising the use of at least one helper oligonucleotide selected from the group consisting of: SEQ ID NOs: 25 and 27.

8. The method of claim 6, further comprising the step of amplifying said *Coccidioides immitis* target nucleic acid prior to said step (a).

9. The method of claim 8, wherein said amplifying uses an amplification oligonucleotide from 15 to 100 nucleotides in length able, under nucleic acid amplification conditions, to bind to or extend through a nucleotide base sequence selected from the group consisting of SEO ID NOs. 10, 12, 30, 32, 34, 36, 38 and 40.

10. The method of claim 9, wherein said oligonucleotide comprises a sequence selected from the group consisting of: SEQ ID NOs: 5, 33, and 35.

11. The method of claim 9, wherein said oligonucleotide comprises a sequence selected from the group consisting of: SEQ ID NOs: 13, 37, and 39.

12. The method of claim 9, wherein said sample is a clinical sample and said method is used to detect and distinguish *Coccidioides immitis* from *Histoplasma capsulatum, Blastomyces dermatitidis, Oidiodendron echinulatum*, and *Malbranchea dendriticus*, if present, directly from a clinical specimen.

13. The method of claim 8, wherein said amplifying uses an amplification oligonucleotide consisting of a 22–100 base sequence having a nucleotide sequence selected from the group consisting of: SEQ ID NOs: 29, 31, 33, 35, 37, and 39.

14. The method of claim 13, wherein said amplification oligonucleotide further comprises at its 5' end a nucleic acid sequence recognized by an RNA polymerase or which enhances initiation or elongation by an RNA polymerase.

15. The method of claim 9, wherein said amplification oligonucleotide is recognized by said RNA polymerase.

16. A method for detecting the presence of *Coccidioides immitis* in a test sample and distinguishing said *Coccidioides immitis* from *Histoplasma capsulatum* and *Blastomyces dermatitidis*, comprising the steps of:

(a) amplifying *Coccidioides immitis* target nucleic acid in a test sample using an amplification oligonucleotide consisting of a 22–100 base sequence having a nucleotide sequence selected from the group consisting of: SEQ ID NOs: 29, 31, 33, 35, 37, and 39;

(b) contacting the amplified target nucleic acid under stringent hybridization assay conditions with a nucleic acid hybridization assay probe which forms a hybrid stable for detection under stringent hybridization conditions with *Coccidioides immitis* nucleic acid, and said probe consisting of a 22–100 base sequence having a nucleotide sequence selected from the group consisting of: SEQ ID NOs:21, 22, 23, and 24;

wherein said probe can distinguish *Coccidioides immitis* nucleic acid from *Histoplasma capsulatum* and *Blas-*

*tomyces dermatitidis* nucleic acid under stringent hybridization assay conditions; and (c) measuring a presence or amount of said hybrid stable for detection.

17. The method of claim 9, wherein said amplification oligonucleotide comprises a sequence selected from the group consisting of: SEQ ID NOs: 1, 5, 13, 29, 31, 33, 35, 37, and 39.

18. The nucleic acid hybridization assay probe of claim 2, wherein said detectable label is an acridinium ester.

19. A probe mix comprising;

a) a nucleic acid hybridization assay probe for detection of *Coccidioides immitis*, comprising a nucleic acid 22–100 nucleotide bases in length comprising a nucleotide sequence selected from the group consisting of: SEQ ID NOs: 21, 22, 23, and 24; wherein said probe distinguishes *Coccidioides immitis* nucleic acid from *Histoplasma capsulatum* and *Blastomyces dermatitidis* nucleic acid under stringent hybridization assay conditions, and b) a helper probe.

20. An amplification oligonucleotide from 15 to 100 nucleotides in length able, under nucleic acid amplification conditions, to bind to or extend through a nucleotide base sequence selected from the group consisting of SEQ ID NOs. 10, 12, 30, 32, 34, and 36.

21. The amplification oligonucleotide of claim 20 from 15 to 50 nucleotides in length.

22. The amplification oligonucleotide of claim 20, comprising a contiguous nucleotide sequence selected from the group consisting of SEQ ID NOs. 9, 11, 29, 31, 33, and 35.

23. The amplification oligonucleotide of claim 20, consisting of a contiguous nucleotide sequence selected from the group consisting of SEQ ID NOs. 9, 11, 29, 31, 33, and 35.

24. The amplification oligonucleotide of claim 20 which comprises, in the 5' upstream region, an oligonucleotide sequence which is recognizable by an RNA polymerase and enhances initiation or elongation by said RNA polymerase.

25. The amplification oligonucleotide of claim 24, wherein said oligonucleotide sequence recognizable by an RNA polymerase comprises SEQ ID NO. 41.

26. The amplification oligonucleotide of claim 25, comprising a sequence selected from the group consisting of SEQ ID NOs. 1, 5 and 13.

27. The amplification oligonucleotide of claim 25, consisting of a sequence selected from the group consisting of SEQ ID NOs. 1, 5 and 13.

28. A composition for amplifying or detecting *Coccidioides immitis* nucleic acid, comprising at least one oligonucleotide selected from the group consisting of:

(a) a first oligonucleotide from 15 to 100 nucleotides in length which will hybridize to at least a portion of a first region of *Coccidioides immitis* nucleic acid, wherein said first region consists of a contiguous nucleotide sequence selected from the group consisting of SEQ ID NOs. 30, 32, 34, 36, 38 and 40; and (b) a second oligonucleotide from 15 to 100 nucleotides in length which will hybridize to at least a portion of a second region of *Coccidioides immitis* nucleic acid, wherein said second region consists of a contiguous nucleotide sequence selected from the group consisting of SEQ ID NOs. 10 and 12.

29. The composition of claim 28, wherein said first oligonucleotide comprises a contiguous nucleotide sequence selected from the group consisting of SEQ ID NOs. 29, 31, 33, 35, 37, and 39 and said second oligonucleotide comprises a contiguous nucleotide sequence selected from the group consisting of SEQ ID NOs. 9 and 11.

30. The composition of claim 28, wherein at least one of said first oligonucleotide or said second oligonucleotide further comprises, in the 5' upstream region, an oligonucleotide sequence which is recognizable by an RNA polymerase and enhances initiation or elongation by said RNA polymerase.

31. The composition of claim 30, wherein said oligonucleotide sequence recognizable by an RNA polymerase comprises SEQ ID NO. 41.

32. The composition of claim 31, wherein said first oligonucleotide comprises a contiguous nucleotide sequence selected from the group consisting of SEQ ID NOs. 1, 5 and 13.

33. The composition of claim 28, further comprising a nucleic acid hybridization probe which comprises a third oligonucleotide from 15 to 100 nucleotides in length which will hybridize with a region of *Coccidioides immitis* nucleic acid to form a detectable hybridization duplex under selective hybridization conditions, wherein said region consists of a contiguous nucleotide sequence selected from the group consisting of SEQ ID NOs. 17 and 21, and their fully complementary sequences of the same length.

34. The composition of claim 33, wherein said third oligonucleotide comprises a contiguous nucleotide sequence selected from the group consisting of SEQ ID NOs. 17 and 21, and their fully complementary sequences of the same length.

35. The composition of claim 33, wherein said third oligonucleotide consists of a contiguous nucleotide sequence selected from the group consisting of SEQ ID NOs. 17 and 21, and their fully complementary sequences of the same length.

36. The composition of claim 33, wherein said first oligonucleotide consists of SEQ ID NO. 1, 5, or 13, said second oligonucleotide consists of SEQ ID NO. 9, and said third oligonucleotide consists of SEQ ID NO. 17 or 21.

37. The composition of claim 33, wherein said probe contains a detectable label.

38. The composition of claim 37, wherein said detectable label is an acridinium ester.

39. The composition of claim 28, further comprising at least one helper oligonucleotide.

40. The composition of claim 38, wherein said helper oligonucleotide consists of SEQ ID NO. 25 or 27.

* * * * *

SEQUENCE LISTING ( 1 ) GENERAL INFORMATION:

( i i i ) NUMBER OF SEQUENCES: 41

( 2 ) INFORMATION FOR SEQ ID NO: 1:

( i ) SEQUENCE CHARACTERISTICS:
( A ) LENGTH: 51
( B ) TYPE: nucleic acid
( C ) STRANDEDNESS: single
( D ) TOPOLOGY: linear ( i i ) SEQUENCE DESCRIPTION: SEQ ID NO: 1:

AATTTAATAC GACTCACTAT AGGGAGAGTC CAGCAGCCAC AGACGGGATT 50

C 51

( 2 ) INFORMATION FOR SEQ ID NO: 2:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) SEQUENCE DESCRIPTION: SEQ ID NO: 2:

GAATCCCGTC TGTGGCTGCT GGACTCTCCC TATAGTGAGT CGTATTAAAT 50

T 51

( 2 ) INFORMATION FOR SEQ ID NO: 3:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) SEQUENCE DESCRIPTION: SEQ ID NO: 3:

AAUUUAAUAC GACUCACUAU AGGGAGAGUC CAGCAGCCAC AGACGGGAUU 50

C 51

( 2 ) INFORMATION FOR SEQ ID NO: 4:

( i ) SEQUENCE CHARACTERISTICS:
( A ) LENGTH: 51 base pairs
( B ) TYPE: nucleic acid
( C ) STRANDEDNESS: single
( D ) TOPOLOGY: linear ( i i ) SEQUENCE DESCRIPTION: SEQ ID NO: 4:

-continued

GAAUCCCGUC UGUGGCUGCU GGACUCUCCC UAUAGUGAGU CGUAUUAAAU 50

U 51

(2) INFORMATION FOR SEQ ID NO: 5:

(i) SEQUENCE CHARACTERISTICS:
(A) LENGTH: 49 base pairs
(B) TYPE: nucleic acid
(C) STRANDEDNESS: single
(D) TOPOLOGY: linear (ii) SEQUENCE DESCRIPTION: SEQ ID NO: 5:

AATTTAATAC GACTCACTAT AGGGAGACAC AGACGGGATT CTCACCCTC 49

(2) INFORMATION FOR SEQ ID NO: 6:

(i) SEQUENCE CHARACTERISTICS:
(A) LENGTH: 49 base pairs
(B) TYPE: nucleic acid
(C) STRANDEDNESS: single
(D) TOPOLOGY: linear (ii) SEQUENCE DESCRIPTION: SEQ ID NO: 6:

GAGGGTGAGA ATCCCGTCTG TGTCTCCCTA TAGTGAGTCG TATTAAATT 49

(2) INFORMATION FOR SEQ ID NO: 7:

(i) SEQUENCE CHARACTERISTICS:
(A) LENGTH: 49 base pairs
(B) TYPE: nucleic acid
(C) STRANDEDNESS: single
(D) TOPOLOGY: linear (ii) SEQUENCE DESCRIPTION: SEQ ID NO: 7:

AAUUUAAUAC GACUCACUAU AGGGAGACAC AGACGGGAUU CUCACCCUC 49

(2) INFORMATION FOR SEQ ID NO: 8:

(i) SEQUENCE CHARACTERISTICS:
(A) LENGTH: 49 base pairs
(B) TYPE: nucleic acid
(C) STRANDEDNESS: single
(D) TOPOLOGY: linear (ii) SEQUENCE DESCRIPTION: SEQ ID NO: 8:

GAGGGUGAGA AUCCCGUCUG UGUCUCCCUA UAGUGAGUCG UAUUAAAUU 49

(2) INFORMATION FOR SEQ ID NO: 9:

(i) SEQUENCE CHARACTERISTICS:
(A) LENGTH: 30 base pairs
(B) TYPE: nucleic acid
(C) STRANDEDNESS: single
(D) TOPOLOGY: linear (ii) SEQUENCE DESCRIPTION: SEQ ID NO: 9:

GCTCAAATTT GAAATCTGTC CATGCGGAGC 30

(2) INFORMATION FOR SEQ ID NO: 10:

(i) SEQUENCE CHARACTERISTICS:
(A) LENGTH: 30 base pairs
(B) TYPE: nucleic acid
(C) STRANDEDNESS: single
(D) TOPOLOGY: linear (ii) SEQUENCE DESCRIPTION: SEQ ID NO: 10:

-continued

GCTCCGCATG GACAGATTTC AAATTTGAGC 30

( 2 ) INFORMATION FOR SEQ ID NO: 11:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) SEQUENCE DESCRIPTION: SEQ ID NO: 11:

GCUCAAAUUU GAAAUCUGUC CAUGCGGAGC 30

( 2 ) INFORMATION FOR SEQ ID NO: 12:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) SEQUENCE DESCRIPTION: SEQ ID NO: 12:

GCUCCGCAUG GACAGAUUUC AAAUUUGAGC 30

( 2 ) INFORMATION FOR SEQ ID NO: 13:

( i ) SEQUENCE CHARACTERISTICS:
( A ) LENGTH: 53
( B ) TYPE: nucleic acid
( C ) STRANDEDNESS: single
( D ) TOPOLOGY: linear ( i i ) SEQUENCE DESCRIPTION: SEQ ID NO: 13:

AATTTAATAC GACTCACTAT AGGGAGAGGA TTCTCACCCT CTATGACGTC 50

CTG 53

( 2 ) INFORMATION FOR SEQ ID NO: 14:

( i ) SEQUENCE CHARACTERISTICS:
( A ) LENGTH: 53
( B ) TYPE: nucleic acid
( C ) STRANDEDNESS: single
( D ) TOPOLOGY: linear ( i i ) SEQUENCE DESCRIPTION: SEQ ID NO: 14:

CAGGACGTCA TAGAGGGTGA GAATCCTCTC CCTATAGTGA GTCGTATTAA 50

ATT 53

( 2 ) INFORMATION FOR SEQ ID NO: 15:

( i ) SEQUENCE CHARACTERISTICS:
( A ) LENGTH: 53
( B ) TYPE: nucleic acid
( C ) STRANDEDNESS: single
( D ) TOPOLOGY: linear ( i i ) SEQUENCE DESCRIPTION: SEQ ID NO: 15:

AAUUUAAUAC GACUCACUAU AGGGAGAGGA UUCUCACCCU CUAUGACGUC 50

CUG 53

( 2 ) INFORMATION FOR SEQ ID NO: 16:

( i ) SEQUENCE CHARACTERISTICS:
( A ) LENGTH: 53
( B ) TYPE: nucleic acid
( C ) STRANDEDNESS: single -continued ( D ) TOPOLOGY: linear ( i i ) SEQUENCE DESCRIPTION: SEQ ID NO: 16:

CAGGACGUCA UAGAGGGUGA GAAUCCUCUC CCUAUAGUGA GUCGUAUUAA 50

AUU 53

( 2 ) INFORMATION FOR SEQ ID NO: 17:

( i ) SEQUENCE CHARACTERISTICS:
( A ) LENGTH: 23
( B ) TYPE: nucleic acid
( C ) STRANDEDNESS: single
( D ) TOPOLOGY: linear ( i i ) SEQUENCE DESCRIPTION: SEQ ID NO: 17:

GCAGCCACGG CATAAGTTCC TTG 23

( 2 ) INFORMATION FOR SEQ ID NO: 18:

( i ) SEQUENCE CHARACTERISTICS:
( A ) LENGTH: 23
( B ) TYPE: nucleic acid
( C ) STRANDEDNESS: single
( D ) TOPOLOGY: linear ( i i ) SEQUENCE DESCRIPTION: SEQ ID NO: 18:

CAAGGAACTT ATGCCGTGGC TGC 23

( 2 ) INFORMATION FOR SEQ ID NO: 19:

( i ) SEQUENCE CHARACTERISTICS:
( A ) LENGTH: 23
( B ) TYPE: nucleic acid
( C ) STRANDEDNESS: single
( D ) TOPOLOGY: linear ( i i ) SEQUENCE DESCRIPTION: SEQ ID NO: 19:

GCAGCCACGG CAUAAGUUCC UUG 23

( 2 ) INFORMATION FOR SEQ ID NO: 20:

( i ) SEQUENCE CHARACTERISTICS:
( A ) LENGTH: 23
( B ) TYPE: nucleic acid
( C ) STRANDEDNESS: single
( D ) TOPOLOGY: linear ( i i ) SEQUENCE DESCRIPTION: SEQ ID NO: 20:

CAAGGAACUU AUGCCGUGGC UGC 23

( 2 ) INFORMATION FOR SEQ ID NO: 21:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 21:

GCGCCACGGC ATAAGTTCCT TG 22

( 2 ) INFORMATION FOR SEQ ID NO: 22:

( i ) SEQUENCE CHARACTERISTICS:
( A ) LENGTH: 22
( B ) TYPE: nucleic acid
( C ) STRANDEDNESS: single -continued ( D ) TOPOLOGY: linear ( i i ) SEQUENCE DESCRIPTION: SEQ ID NO: 22:

CAAGGAACTT ATGCCGTGGC GC 22

( 2 ) INFORMATION FOR SEQ ID NO: 23:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 23:

GCGCCACGGC AUAAGUUCCU UG 22

( 2 ) INFORMATION FOR SEQ ID NO: 24:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 24:

CAAGGAACUU AUGCCGUGGC GC 22

( 2 ) INFORMATION FOR SEQ ID NO: 25:

( i ) SEQUENCE CHARACTERISTICS:
( A ) LENGTH: 29
( B ) TYPE: nucleic acid
( C ) STRANDEDNESS: single
( D ) TOPOLOGY: linear ( i i ) SEQUENCE DESCRIPTION: SEQ ID NO: 25:

GAACAGGACG TCATAGAGGG TGAGAATCC 29

( 2 ) INFORMATION FOR SEQ ID NO: 26:

( i ) SEQUENCE CHARACTERISTICS:
( A ) LENGTH: 29
( B ) TYPE: nucleic acid
( C ) STRANDEDNESS: single
( D ) TOPOLOGY: linear ( i i ) SEQUENCE DESCRIPTION: SEQ ID NO: 26:

GGATTCTCAC CCTCTATGAC GTCCTGTTC 29

( 2 ) INFORMATION FOR SEQ ID NO: 27:

( i ) SEQUENCE CHARACTERISTICS:
( A ) LENGTH: 29
( B ) TYPE: nucleic acid
( C ) STRANDEDNESS: single
( D ) TOPOLOGY: linear ( i i ) SEQUENCE DESCRIPTION: SEQ ID NO: 27:

GAACAGGACG UCAUAGAGGG UGAGAAUCC 29

( 2 ) INFORMATION FOR SEQ ID NO: 28:

( i ) SEQUENCE CHARACTERISTICS:
( A ) LENGTH: 29
( B ) TYPE: nucleic acid
( C ) STRANDEDNESS: single
( D ) TOPOLOGY: linear ( i i ) SEQUENCE DESCRIPTION: SEQ ID NO: 28:

GGAUUCUCAC CCUCUAUGAC GUCCUGUUC 29

( 2 ) INFORMATION FOR SEQ ID NO: 29:

( i ) SEQUENCE CHARACTERISTICS:
( A ) LENGTH: 24
( B ) TYPE: nucleic acid
( C ) STRANDEDNESS: single
( D ) TOPOLOGY: linear ( i i ) SEQUENCE DESCRIPTION: SEQ ID NO: 29:

GTCCAGCAGC CACAGACGGG ATTC 24

( 2 ) INFORMATION FOR SEQ ID NO: 30:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) SEQUENCE DESCRIPTION: SEQ ID NO: 30:

GAATCCCGTC TGTGGCTGCT GGAC 24

( 2 ) INFORMATION FOR SEQ ID NO: 31:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) SEQUENCE DESCRIPTION: SEQ ID NO: 31:

GUCCAGCAGC CACAGACGGG AUUC 24

( 2 ) INFORMATION FOR SEQ ID NO: 32:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) SEQUENCE DESCRIPTION: SEQ ID NO: 32:

GAAUCCCGUC UGUGGCUGCU GGAC 24

( 2 ) INFORMATION FOR SEQ ID NO: 33:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO: 33:

CACAGACGGG ATTCTCACCC TC 22

( 2 ) INFORMATION FOR SEQ ID NO: 34:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO: 34:

-continued

GAGGGTGAGA ATCCCGTCTG TG 22

( 2 ) INFORMATION FOR SEQ ID NO: 35:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO: 35:

CACAGACGGG AUUCUCACCC UC 22

( 2 ) INFORMATION FOR SEQ ID NO: 36:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) SEQUENCE DESCRIPTION: SEQ ID NO: 36:

GAGGGUGAGA AUCCCGUCUG UG 22

( 2 ) INFORMATION FOR SEQ ID NO: 37:

( i ) SEQUENCE CHARACTERISTICS:
( A ) LENGTH: 26
( B ) TYPE: nucleic acid
( C ) STRANDEDNESS: single
( D ) TOPOLOGY: linear ( i i ) SEQUENCE DESCRIPTION: SEQ ID NO: 37:

GGATTCTCAC CCTCTATGAC GTCCTG 26

( 2 ) INFORMATION FOR SEQ ID NO: 38:

( i ) SEQUENCE CHARACTERISTICS:
( A ) LENGTH: 26
( B ) TYPE: nucleic acid
( C ) STRANDEDNESS: single
( D ) TOPOLOGY: linear ( i i ) SEQUENCE DESCRIPTION: SEQ ID NO: 38:

CAGGACGTCA TAGAGGGTGA GAATCC 26

( 2 ) INFORMATION FOR SEQ ID NO: 39:

( i ) SEQUENCE CHARACTERISTICS:
( A ) LENGTH: 26
( B ) TYPE: nucleic acid
( C ) STRANDEDNESS: single
( D ) TOPOLOGY: linear ( i i ) SEQUENCE DESCRIPTION: SEQ ID NO: 39:

GGAUUCUCAC CCUCUAUGAC GUCCUG 26

( 2 ) INFORMATION FOR SEQ ID NO: 40:

( i ) SEQUENCE CHARACTERISTICS:
( A ) LENGTH: 26
( B ) TYPE: nucleic acid
( C ) STRANDEDNESS: single
( D ) TOPOLOGY: linear ( i i ) SEQUENCE DESCRIPTION: SEQ ID NO: 40:

CAGGACGUCA UAGAGGGUGA GAAUCC 26

-continued ( 2 ) INFORMATION FOR SEQ ID NO: 41:

( i ) SEQUENCE CHARACTERISTICS:
( A ) LENGTH: 27
( B ) TYPE: nucleic acid
( C ) STRANDEDNESS: single
( D ) TOPOLOGY: linear ( i i ) SEQUENCE DESCRIPTION: SEQ ID NO: 41:

AATTTAATAC GACTCACTAT AGGGAGA 27